(12) United States Patent
Falchuk

(10) Patent No.: US 6,908,732 B2
(45) Date of Patent: Jun. 21, 2005

(54) COMPOUNDS AND METHODS FOR REGULATING CELL DIFFERENTIATION

(75) Inventor: Kenneth H. Falchuk, Newton, MA (US)

(73) Assignee: President & Fellows of Harvard College, Cambridge, MA (US)

(*) Notice: Subject to any disclaimer, the term of this patent is extended or adjusted under 35 U.S.C. 154(b) by 441 days.

(21) Appl. No.: 09/977,866

(22) Filed: Oct. 15, 2001

(65) Prior Publication Data

US 2002/0099085 A1 Jul. 25, 2002

Related U.S. Application Data

(60) Provisional application No. 60/240,497, filed on Oct. 13, 2000.

(51) Int. Cl.[7] .......................... A01N 1/00; A01N 43/38; C12N 5/02; A61K 31/409
(52) U.S. Cl. ........................ 435/1.1; 435/325; 514/359; 514/422
(58) Field of Search .................. 435/1.1, 325; 514/359, 514/422

(56) References Cited

U.S. PATENT DOCUMENTS

| | | | |
|---|---|---|---|
| 4,353,888 A | 10/1982 | Sefton | 424/25 |
| 4,892,538 A | 1/1990 | Aebischer et al. | 604/891.1 |
| 4,955,892 A | 9/1990 | Daniloff | 606/152 |
| 5,041,138 A | 8/1991 | Vacanti et al. | 623/16 |
| 5,092,871 A | 3/1992 | Aebischer et al. | 606/152 |
| 5,106,627 A | 4/1992 | Aebischer et al. | 424/424 |
| 5,288,514 A | 2/1994 | Ellman | 427/2 |
| 5,359,115 A | 10/1994 | Campbell et al. | 558/110 |
| 5,362,899 A | 11/1994 | Campbell | 558/108 |
| 5,712,171 A | 1/1998 | Zambias et al. | 436/518 |

FOREIGN PATENT DOCUMENTS

| | | |
|---|---|---|
| JP | 3047166 | 2/1991 |
| JP | 6183969 | 7/1994 |
| WO | WO 91/07087 | 5/1991 |
| WO | WO 92/10092 | 6/1992 |
| WO | WO 93/01275 | 1/1993 |
| WO | WO 93/09668 | 5/1993 |
| WO | WO 93/20242 | 10/1993 |
| WO | WO 94/08051 | 4/1994 |
| WO | WO 94/09119 | 4/1994 |
| WO | WO 94/10292 | 5/1994 |
| WO | WO 94/16718 | 8/1994 |
| WO | WO 95/18856 | 7/1995 |
| WO | WO 96/17924 | 6/1996 |
| WO | WO 01/82932 | 11/2001 |
| WO | WO 01/96345 | 12/2001 |

OTHER PUBLICATIONS

Janes et al. "Role of hyperbilirubinemia . . . " J. Clin. Invest. (1995) 95(6): 2851–6.*
Rhine et al. "Bilirubin Toxicity . . . " J. Perinatol. (1999) 19(3): 206–211.*
Notter et al. "Differential Sensitivity of . . . " (1986) 94:670–682.*
Webster's II New Riverside Dictionary (1984) Houghton-–Mifflin: Boston, pp. 762 and 990.*
Sima et al. "The Suppressive Effect . . . " Folia Microbiol. (1980) 25:483–490.*

(Continued)

Primary Examiner—Jean C. Witz
Assistant Examiner—Susan Hanley
(74) Attorney, Agent, or Firm—Banner & Witcoff, Ltd.

(57) ABSTRACT

The present invention makes available methods and reagents for inhibiting cell growth or promoting cell differentiation comprising contacting the cell with a differeguline in a sufficient amount to inhibit cell proliferation or promote cell differentiation.

9 Claims, 12 Drawing Sheets

OTHER PUBLICATIONS

Nakajima et al. "Eryththroid Differentiation–Inducing Activity . . . " Biochem. Biophys. Res. Comm. (1994) 198(2): 720–727.*

Janes et al., "Bilirubin Inhibits Proliferation in Cultured Normal Human Osteoblast–Like Cells: . . . ," abstract from *Gastrointerology*, 102(4) part 2, p. A827, #XP00801667 (1992).

Peters and Wiley, "Evidence that Murine Preimplantation Embryos Express Aryl Hydrocarbon Receptor," *Toxicology and Applied Pharmacology*, 134:214–221 (1995).

Phelan et al., "Activation of the Ah Receptor Signal Transduction Pathway by Bilirubin and Biliverdin," *Arch. Biochem. and Biophys.*, 357(1):155–163 (1998).

Thaler, "Bilirubin Toxicity in Hepatoma Cells," *Nature: New Biology*, 230(15):218–219 (1971).

Vassilopoulou–Sellin et al., "Bilirubin as an Inhibitor of Cartilage Metabolism: Effect on Avian Chondrocyte Proliferation in Cell Culture," *J. Bone and Mineral Res.*, 5(7):769–774 (1990).

Zaher et al., "The Involvement of Aryl Hydrocarbon Receptor in the Activation of Transforming Growth Factor–β and Adoptosis," *Mol. Pharm.*, 54:313–321 (1998).

Zhou et al., "Photosensitization of bilirubin on proliferation and DNA synthesis in ascitic hepatoma cells," *Acta Pharm. Sinica*, 17(2):164–166 (1996).

Zucker et al., "Inhibition of Breast Cancer Cell Proliferation by Unconjugated Bilirubin . . . ," abstract from *Hepatology*, 30(4) part 2, p. 498A, XP008016620 (1999).

English abstract of Chinese Patent No. CN 1185956 (XP–002240175).

English abstract of Japanese Patent No. JP 53081611 (XP–002240174).

English abstract of Japanese Patent No. JP 3047166 (XP–002240176).

English abstract of Japanese Patent No. JP 6183969 (XP–002240177).

Achkar et al., "4–Oxoretinol, a new natural ligand and transactivator of the retinoic acid receptors," *Proc. National. Acad. Sci., USA*, 93:4879–4884, 1996.

Ang and Rossant, "HNF–3β is Essential for Node and Notochord Formation in Mouse Development," *Cell*, 78:561–574, 1994.

Azuma, "Changes of EGG Retinoids During Development of *Xenopus laevis*," *Vision Res*, 30(10):1395–1400, 1990.

Davidson, "How embryos work: a comparative view of diverse modes of cell fate specification," *Development*, 108:365–389, 1990.

Dawid, "Intercellular Signaling and Gene Regulation during Early Ernbryogenesis of *Xenopus laevis*," *J. Biol. Chem.*, 269:6259–6262, 1994.

Dexter, "N,N–Dimethylformamide–induced Morphological Differentiation and Reduction of Tumorgenicity in Cultured Mouse Rhabdomyosarcoma Cells," *Cancer Res.*, 37:3136–3140, 1977.

Donehower et al., "Mice deficient for p53 are developmentally normal but susceptible to spontaneous tumors," *Nature* 356: 215–221, 1992.

Donehower, "The p53–deficient Mouse: A model for basic and applied cancer studies," *Cancer Biol*. 7:269–278, 1996.

Durston et al., "Retinoic acid causes an anteroposterior transformation in the developing central nervous system," *Nature*, 340:140–144, 1989.

Eichele, "Retinoids and vertebrate limb pattern formation," *Trends in Genetics*, 5:246–251, 1989.

Falchuk et al., "Zinc Uptake and Distribution in *Xenopus laevis* Oocytes and Embryos," *Biochemistry* 34:16524–16531, 1995.

Fearon et al., "Differentiation of Leukemia Cells to Polymorphonuclear Leukocytes in Patients with Acute Nonlymphocytic Leukemia," *N. Eng. J. Med*. 315:15–24, 1986.

Fibach et al., "Effect of Hexamethylene bis acetarnide on the Commitment to Differentiation of Murine Erythro Cells," *Cancer Res.*, 37:440–444, 1977.

Formelli and Cleris, "Synthetic Retinoid Fenretinide is Effective against a Human Ovarian Carcinoma Xenograft and Potentiates Cisplantin Activity," *Cancer Res.* 51:5374–5376, 1993.

Friend et al., "Hemoglobin Synthesis in Murine Virus Induced Leukemia Cells In Vitro: Stimulation of Erythroid Differentiation by Dimethyl Sulfoxide," *Proc. Natl. Acad. Sci. USA*, 69:378–382, 1971.

Gamet et al., "Effects of Short–Chain Fatty Acids on Growth and Differentiation of the Human Colon–Cancer Cell Line HT29," *Int. J. Cancer*, 52:286–289, 1992.

Grant, "Phosphate Metabolism during Oogenesis in *Rana temporaria*," *J. Exp. Zool.*, 124:513–543, 1953.

Grubbs et al., "Inhibition of Mammary Cancer by Retinyl Methyl Ether," *Cancer Res.*, 37:599–602, 1977.

Gum et al., "Effect of Sodium Butyrate on Human Colonic Adenocarcinoma Cells: Induction of Placental–like Alkaline Phosphatase," *J. Biol. Chem.*, 262:1092–1097, 1987.

Gurdon, "The Generation of Divserity and Pattern in Animal Development," *Cell*, 68:185–199, 1992.

Hausen and Riebesell, *The Early Development of Xenopus laeva*. Springer–Verlag, Berlin Heidelberg New York. Plates 7–10, 1991.

Hemmati–Brivanlou et al., "Follistatin, an Antagonist of Activin, Is Expressed in the Spemann Organizer and Displays Direct Neuralizing Activity," *Cell*, 77:283–295, 1994.

Heyman et al., "9–Cis Retinoic Acid Is a High Affinity Ligand for the Retinoid X Receptor," *Cell*, 68:397–406, 1992.

Holwill et al., "Axis and germ line deficiencies caused by u.v. irradiation of Xenopus oocytes cultured in vitro," *Development*, 100:735–743, 1987.

Huberman et al., "Induction of terminal differentiation in human promyelocytic leukemia cells by tumor promoting agents," *Proc. Natl. Acad. Sci. USA*, 76(3):1293–1297, 1971.

Jessell et al., Diffusible Factors in Vertebrate Embryonic Induction, *Cell* 68:257–270, 1992.

Jörnvall. et al., "1,10–Phenanthroline and *Xenopus laevis* Teratology," *Biochem Res. Commun.*, 200(3):1398–1406, 1994.

Kostich and Sanes, "Expression of zfh–4, a New Member of the Zinc Finger–Homeodomain Family, in Developing Brain and Muscle," *Dev. Dynamics*, 202:145–152, 1995.

Kraft and Juchau, "Correlations Between Conceptal Concentrations of All–Trans–Retinoic Acid and Dysmorphogenesis After Microinjections . . . ," *Drug Metab. Dispos.*, 20(2):218–225, 1992.

Krishnaraju et al., "The Zinc Finger Transcription Factor Egr–I Potentiates Macrophage Differentiation of Hematopoietic Cells," *Mol. Cell Biol.*, 15:5499–5507, 1995.

Kühnlein et al., "*Spalt* encodes an evolutionarily conserved zinc finger protein of novel structure which provides homeotic gene gunction . . . ," *Emmo J.*, 13(1):168–179, 1994.

Leid et al., "Multiplicity Generates Diversity in the Retinoic Acid Signaling Pathways," *TIBS*, 427–433, 1992.

Marks et al., "Induction of Transformed Cells to Terminal Differentiation and the Modulation of Gene Expression," *Cancer Res.*, 47:659–666, 1987.

McCarthy et al., "Toxicity and Antitumor Activity of Liposome Entrapped Retinoid," Rol.3–7410, Sel. *Cancer Ther.* 7:151–157, 1991.

Mellerick et al., "*Castor* Encodes a Novel Zinc Finger Protein Required for the Development of a Subset of CNS Neurons in Drosophila," *Neuron* 9:789–803, 1992.

Mendelsohn et al., "Function of the retinoic acid receptors (RARs) during development: (II) Multiple abnormalities . . . ," *Development* 120:2749–2771, 1994.

Mével–Ninio et al., "The ovo gene of Drosophila encodes a zinc finger protein required for female germ line development," Embo J., 10(8):2259–2266, 1991.

Mintz and Ilmensee, "Normal genetically mosaic mice produced from malignant teratocarcinoma cells," *Proc. Natl. Acad Sci. USA*, 72(9):3585–3589, 1975.

Morikawa et al., "Influence of Organ Environment on the Growth, Selection, and Metastasis of Human Colon Carcinoma Cells in Nude Mice," *Cancer Res.* 48:6863–6871, 1988.

Mueller et al., "Terminal Differentiation of Human Breast Cancer through PPARγ," *Mol. Cell*, 1:465–470, 1998.

Nagai et al., "The Expression of the Mouse Zic1, Zic2, and Zic3 Gene Suggests an Essential Role for Zic Genes in Body Pattern Formation," *Dev. Biol.* 182:299–313, 1997.

Nomizu et al., "Zinc, Iron and Copper Content of *X. laevis* oocyte and Embryos," *Mol. Reprod Develop*, 1:314–319, 1993.

Olson et al., "A Monoclonal Antibody to Human Antiogenin Suppresses Tumor Growth in Athymic Mice," *Cancer Research*, 54:4576–4579, 1994.

Perrotti et al., "Overexpression of the Zinc Finger protein MZF1 Inhibits Hematopoietic Development from Embryonic Stem Cells: Correlation with Negative Regulation of *CD34* and *c–rnyb* Promoter Activity," *Mol. Cell. Biol.* 15(11):6075–6097, 1995.

Pfhal, "Retinoids: Concepts for Separation of Desirable and Undesirable Effects in the Treatment or Prevention of Cancer," *Hormones and Cancer.* Ed. Vederlds, Birkhauser, Boston. pp. 127–146, 1996.

Pierce and Speers, "Tumors as Caricatures of the Process of Tissue Renewal: Prospects for Therapy by Directing Differentiation," *Cancer Res.*, 48:1996–2004, 1988.

Pijnappel et al., "The Retinoid ligand 4–oxo–retinoic acid is a highly active modulator of positional specification," *Nature*, 366:340–344, 1993.

Preflow et al., "Transplantation of Human Prostatic Carcinoma into Nude Mice in Matrigel," *Cancer Res.*, 51:3814–3817, 1991.

Redeman et al., "Disruption of a putative Cys–zinc interaction eliminates the biological activity of the *Krüppel* finger protein," *Nature* (London), 332:90–92, 1988.

Roark et al., "Scratch, a pan–neural gene encoding a zinc finger protein related to *snail*, promotes neuronal development," *Genes & Dev.*, 9:2384–2390,1995.

Sarraf et al., "Differentiation and reversal of malignant changes in colon cancer through PPARγ,"*Nature Medicine*, 4:1046–1052, 1998.

Sasai et al., "Xenopus *chordin*: A Novel Dorsalizing Factor Activated by Organizer–Specific Homeobox Genes," *Cell*, 79:779–790,1994.

Scharf and Gerhart, "Determination of the Dorsal–Ventral Axis in Eggs of *Xenopus laevis*: Complete Rescue of uv–Impaired Eggs . . . ,"*Develop. Biol.* 79:181–198, 1980.

Scharf and Gerhart, "Axis Determination in Eggs of *Xenopus laevis*: a Critical Period before First Cleagave . . . ," *Dev. Biol.*, 99:75–87, 1983.

Schleicher et al., "Influence of Retinoids on Growth and Metastasis . . . ," *Cancer Res.*, 48:1465–1469, 1988.

Schubert et al., "Induced Differentiation of a Neuroblastoma," *Dev. Biol.*, 25:514–546, 1971.

Schütz and Niessing, "Cloning and structure of a chicken zinc finger cDNA: restricted expression in developing neural crest cells," *Gene*, 148:227–236, 1994.

Schwartz et al., "Sodium butyrate induces retinoblastoma protein dephosphorylation, p16 expression and growth arrest of colon cancer cells," *Mol. & Cell Biochem.*, 188:21–30, 1993.

Shalinsky et al., "A Novel Retinoic acid Receptor–selective Retinoid, ALRT1550, Has Potent Antitumor Activity . . . ," *Cancer Res*, 57:162–168, 1997.

* cited by examiner

CONTROL

UV EXPOSED

INDEX OF AXIAL DEFICIENCY

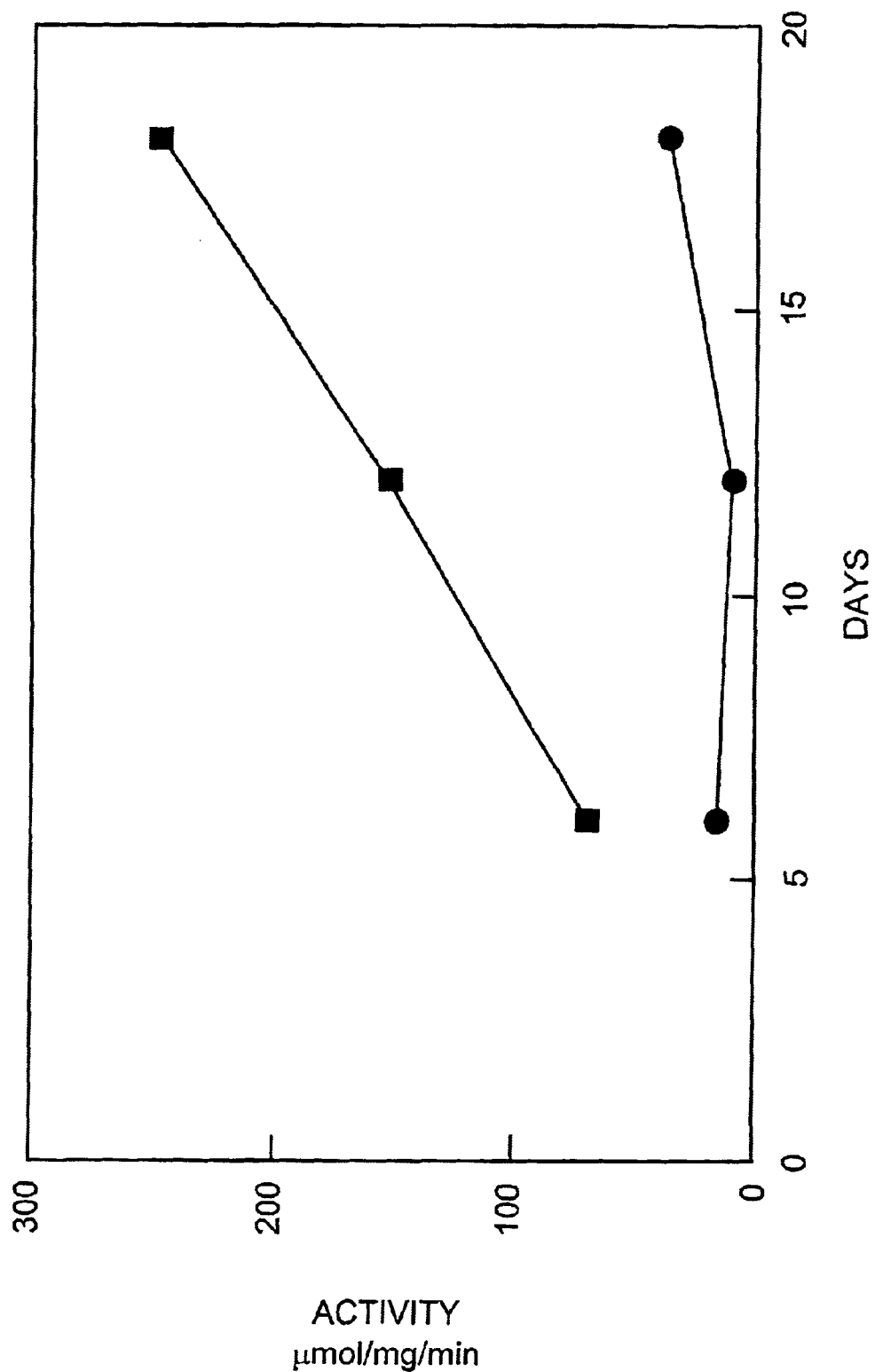

COMPOUNDS AND METHODS FOR REGULATING CELL DIFFERENTIATION

This application claims the benefit of the filing date of U.S. Provisional Application Ser. No. 60/240,497, filed Oct. 13, 2000.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108:365–389; Gurdon, J. B., (1992) *Cell* 68:185–199; Jessell, T. M. et al., (1992) *Cell* 68:257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

SUMMARY OF THE INVENTION

The present invention makes available methods and reagents for inhibiting cell proliferation or promoting cell differentiation comprising contacting the cell with a differeguline in a sufficient amount to inhibit cell proliferation or promote cell differentiation.

The present invention further makes available methods for a number of applications, including the in vivo modulation of lipid metabolism; in vivo modulation of skin related processes (e.g., acne, psoriasis, aging, wrinkling, and the like); in vivo modulation of programmed cell death (apoptosis); in vivo modulation of malignant cell development, such as occurs, for example, in acute promyelocytic leukemia, mammary cancer, prostate cancer, lung cancer, cancers of the aerodigestive pathway, skin cancer, bladder cancer, and sarcomas; in vivo modulation of pre-malignant lesions, such as occurs with oral leukoplakia and the like; in vivo modulation of auto-immune diseases such as rheumatoic arthritis; in vivo modulation of fatty acid metabolism; and the like. Such applications can be expected to allow the modulation of various biological processes with reduced occurrence of undesirable side effects such as teratogenic effects, skin irritation, mucosal dryness, lipid disturbances, and the like. In vivo applications can be employed with a wide range of subjects, such as, for example, humans, rodents, sheep, pigs, cows, dogs, and the like.

BRIEF DESCRIPTION OF THE DRAWINGS

FIG. 10 depicts the effect of 4-oxoRE$_{18}$ on alkaline phosphatase (boxes, circles are control).

Figure 1:
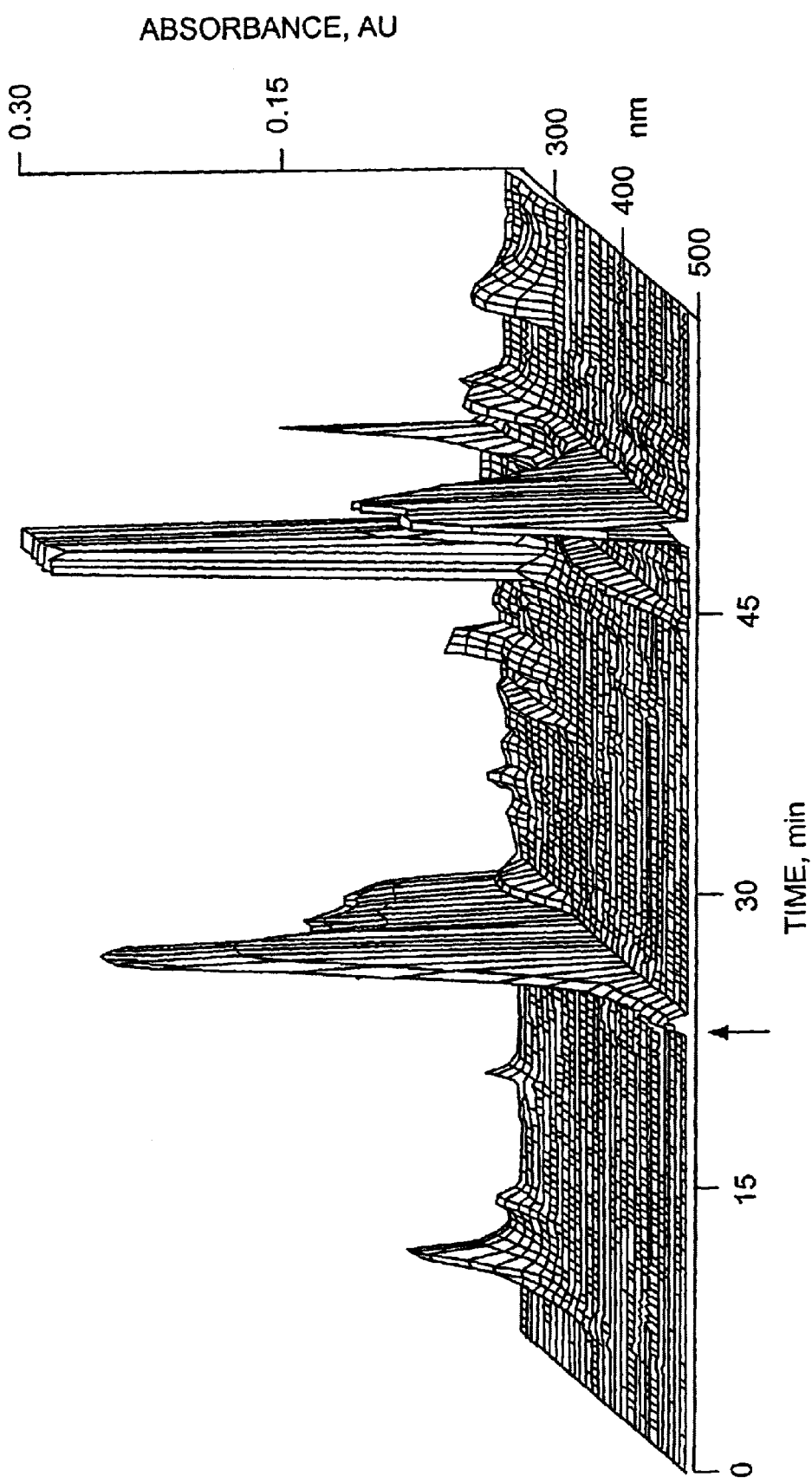
FIG. 1 depicts an elution profile of an extract of oocyte homogenate. The arrow indicates the elution of 4-oxo-retinyl ester.

This application hereby incorporates by reference all Figures filed in U.S. Provisional Application No. 60/128, 653, filed Apr. 8, 1999.

DETAILED DESCRIPTION OF THE INVENTION

I. Overview

Thus, the methods of the present invention include the use of small molecules which inhibit cell proliferation or promote cell differentiation to regulate the repair and/or functional performance of a wide range of cells, tissues and organs. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein). Additionally, the subject methods may be performed on stem cells to promote or regulate a differentiated state in cultured cells.

In another preferred embodiment, the subject method can be used as part of a treatment regimen for unwanted proliferation of transformed cells. For example, a differeguline may be useful for terminal differentiation therapy of a cancerous growth.

In another aspect, the present invention provides pharmaceutical preparations comprising, as an active ingredient, a differeguline such as described herein, formulated in an amount sufficient to inhibit, in vivo, proliferation or promote cell differentiation.

The subject treatments using differegulines can be effective for both human and animal subjects. Animal subjects to which the invention is applicable extend to both domestic animals and livestock, raised either as pets or for commercial purposes. Examples are dogs, cats, cattle, horses, sheep, hogs, and goats.

II. Definitions

For convenience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild-type splicing of mRNA transcribed from the gene.

As employed herein, the phrase "members of the steroid/thyroid superfamily of receptors" (also known as "nuclear receptors" or "intracellular receptors") refers to hormone binding proteins that operate as ligand-dependent transcription factors. Furthermore, this classification includes identified members of the steroid/thyroid superfamily of receptors for which specific ligands have not yet been identified (referred to hereinafter as "orphan receptors"). All members of the intracellular receptor superfamily have the intrinsic ability to bind to specific DNA sequences. Following binding, the transcriptional activity of a target gene (i.e., a gene associated with the specific DNA sequence) is modulated as a function of the ligand bound to the receptor. Also, see Heyman et al., Cell, 68:397–406 (1992), incorporated herein by reference.

An "effective amount" of, e.g., a differeguline, with respect to the subject method of treatment, refers to an amount of the differeguline in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

A "patient" or "subject" to be treated by the subject method can mean either a human or non-human animal.

The "growth state" of a cell refers to the rate of proliferation of the cell and/or the state of differentiation of the cell.

The terms "epithelia", "epithelial" and "epithelium" refer to the cellular covering of internal and external body surfaces (cutaneous, mucous and serous), including the glands and other structures derived therefrom, e.g., corneal, esophegeal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "epidermis" refers to the outermost and nonvascular layer of the skin, derived from the embryonic ectoderm, varying in thickness from 0.07–1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

"Burn wounds" refer to cases where large surface areas of skin have been removed or lost from an individual due to heat and/or chemical agents.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

"Dental tissue" refers to tissue in the mouth which is similar to epithelial tissue, for example gum tissue. The method of the present invention is useful for treating periodontal disease.

The term "nail" refers to the horny cutaneous plate on the dorsal surface of the distal end of a finger or toe.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

As used herein, "proliferating" and "proliferation" refer to cells undergoing mitosis.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

As used herein, "immortalized cells" refers to cells which have been altered via chemical and/or recombinant means such that the cells have the ability to grow through an indefinite number of divisions in culture.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

The term "heteroatom" as used herein means an atom of any element other than carbon or hydrogen. Preferred heteroatoms are boron, nitrogen, oxygen, phosphorus, sulfur and selenium.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$–$C_{30}$ for straight chains, $C_3$–$C_{30}$ for branched chains), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

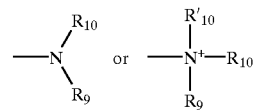

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

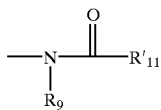

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art-recognized as an amino-substituted carbonyl and includes a moiety that can be represented by the general formula:

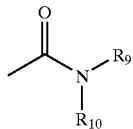

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S-$(CH_2)_m$—$R_8$, wherein m and $R_8$ are defined above. Representative alkylthio groups include methylthio, ethylthio, and the like.

The term "carbonyl" is art-recognized and includes such moieties as can be represented by the general formula:

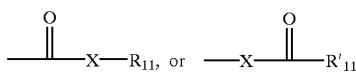

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art-recognized and includes a moiety that can be represented by the general formula:

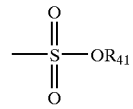

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

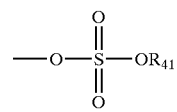

in which $R_{41}$ is as defined above.

The term "sulfonamido" is art-recognized and includes a moiety that can be represented by the general formula:

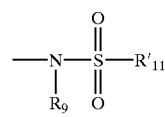

in which $R_9$ and $R'_{11}$ are as defined above.

The term "sulfamoyl" is art-recognized and includes a moiety that can be represented by the general formula:

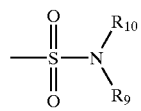

in which $R_9$ and $R_{10}$ are as defined above.

The terms "sulfoxido" or "sulfinyl", as used herein, refers to a moiety that can be represented by the general formula:

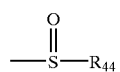

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

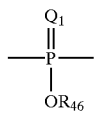

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

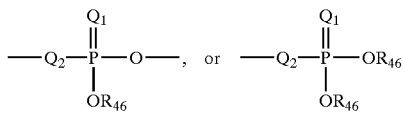

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

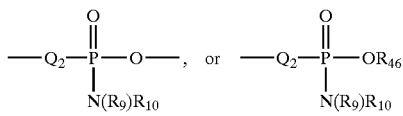

wherein $R_9$ and $R_{10}$ are as defined above, and $Q_2$ represents O, S or N.

A "phosphonamidite" can be represented in the general formula:

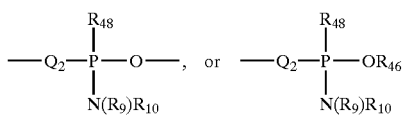

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se-$(CH_2)_m$—$R_8$, m and $R_8$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit cell proliferation or promote cell differentiation), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The term "$ED_{50}$" means the dose of a drug which produces 50% of its maximum response or effect. Alternatively, "$ED_{50}$" may mean the dose which produces a predetermined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

III. Exemplary Compounds of the Invention

As described in further detail below, it is contemplated that the subject methods can be carried out using a variety of different small molecules which can be readily identified, for example, by such drug screening assays as described herein. For example, compounds useful in the subject methods include bilins. Bilins are a class of compound which include at least 3, optionally 4 or 5, substituted or unsubstituted nitrogen-containing five-membered rings, each ring separated from the next by a single carbon, wherein the carbons in the five-membered rings, and optionally some or all of the carbons which connect two rings, are unsaturated. Thus, bilins include compounds represented by general formula (I):

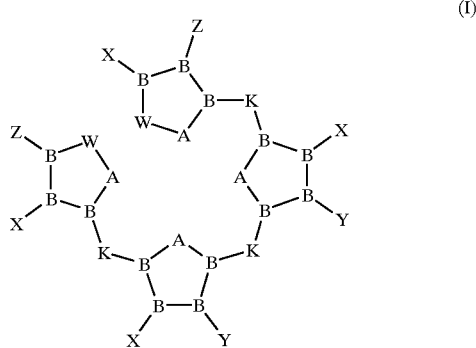

(I)

wherein W represents —$CL_2$—, —C(=O)—, —C(=S)—, —C(=NH)—, or =CL—, preferably —C(=O)—, =CL—, —C(=NH)—, or —C(=S)—, even more preferably —C(=O)—, or —C(=S)—;

X represents a substituted or unsubstituted alkyl, alkenyl, or alkynyl group, preferably a lower alkyl group such as methyl, ethyl, etc.

Y represents a substituted or unsubstituted alkyl, alkenyl, or alkynyl group, optionally substituted with a carboxylic acid moiety, such as a carboxymethylene, carboxypropylene, etc.;

Z represents a substituted or unsubstituted alkyl, alkenyl, or alkynyl group, preferably a lower alkyl group such as vinyl, propenyl, butenyl, etc.;

A represents —NH— or —N=;

B represents a trisubstituted, sp$^2$-hybridized carbon atom;

K represents =CL— or —$CL_2$—; and

L represents H or lower alkyl, preferably H.

In certain embodiments, the compound is biliverdine. In certain other embodiments, the compound is bilirubin.

In certain preferred embodiments, the subject inhibitors inhibit cell proliferation or promote cell differentiation with an $ED_{50}$ of 1 mM or less, more preferably of 1 $\mu$M or less, and even more preferably of 1 nM or less.

In certain embodiments, compounds of the present invention may be used in conjunction with apoptosis-inducing compounds thereby increasing their effect.

IV. Exemplary Applications of Method and Compositions

Another aspect of the present invention relates to a method of modulating a differentiated state, survival, and/or proliferation of a cell by contacting the cell with a differeguline according to the subject method and as the circumstances may warrant.

For instance, it is contemplated by the invention that, in light of the findings of an apparently broad involvement differegulines in the formation of ordered spatial arrangements of differentiated tissues in vertebrates, the subject method could be used as part of a process for generating and/or maintaining an array of different vertebrate tissue both in vitro and in vivo. The differeguline, whether inductive or anti-inductive with respect proliferation or differentiation of a given tissue, can be, as appropriate, any of the preparations described above.

For example, the present method is applicable to cell culture techniques. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such sultures for the generation of new neurons and glia. In such embodiments of the subject method, the cultured cells can be contacted with a differeguline of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motorneurons. Such neuronal cultures can be used as convenient assay systems as well as sources of implantable cells for therapeutic treatments.

According to the present invention, large numbers of non-tumorigenic neural progenitor cells can be perpetuated in vitro and their rate of proliferation and/or differentiation can be effected by contact with differegulines of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a differeguline.

Progenitor cells are thought to be under a tonic inhibitory influence which maintains the progenitors in a suppressed state until their differentiation is required. However, recent techniques have been provided which permit these cells to be proliferated, and unlike neurons which are terminally differentiated and therefore non-dividing, they can be produced in unlimited number and are highly suitable for transplantation into heterologous and autologous hosts with neurodegenerative diseases.

By "progenitor" it is meant an oligopotent or multipotent stem cell which is able to divide without limit and, under specific conditions, can produce daughter cells which terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, in particular during epilepsy surgery, and more particularly during temporal lobectomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument or by mincing with a scalpel to a allow outgrowth of specific cell types from a tissue. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6–8, more preferably close to pH 7, even more particularly about pH 7.4. Cells should be cultured at a temperature close to physiological temperature, preferably between 30° C.–40° C., more preferably between 32° C.–38° C., and most preferably between 35° C.–37° C.

Cells can be grown in suspension or on a fixed substrate, but proliferation of the progenitors is preferably done in suspension to generate large numbers of cells by formation of "neurospheres" (see, for example, Reynolds et al. (1992) *Science* 255:1070–1709; and PCT Publications WO93/01275, WO 94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 3–4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3–10 days in vitro, the proliferating clusters (neurospheres) are fed every 2–7 days, and more particularly every 2–4 days by gentle centrifugation and resuspension in medium containing growth factor.

After 6–7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be control in culture by plating (or resuspending) the cells in the presence of a differeguline.

To further illustrate other uses of the subject differegulines, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265–289; and Freund et al. (1985) *J Neurosci* 5:603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of differegulines employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The differegulines can be used alone, or can be used in combination with other neurotrophic factors which act to more particularly enhance a particular differentiation fate of the neuronal progenitor cell.

In addition to the implantation of cells cultured in the presence of the subject differegulines, yet another aspect of the present invention concerns the therapeutic application of a differeguline to regulate the growth state of neurons and other neuronal cells in both the central nervous system and the peripheral nervous system.

As appropriate, the subject method can also be used in generating nerve prostheses for the repair of central and peripheral nerve damage. In particular, where a crushed or severed axon is intubulated by use of a prosthetic device, differegulines can be added to the prosthetic device to regulate the rate of growth and regeneration of the dendridic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the differeguline can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Those arising in the supratentorial region generally fare worse than their PF counterparts.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ¾ were histologically benign. Approximately ⅔ arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that differegulines are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising differegulines can also be utilized for both cell culture and therapeutic methods involving generation and maintenance of non-neuronal tissue.

In one embodiment, the present invention makes use of differegulines for controlling the development of stem cells responsible for formation of the digestive tract, liver, lungs, and other organs which derive from the primitive gut. Therefore, for example, differegulines of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of differegulines can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising differegulines can be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodernal cells. In the context of the present invention, it is contemplated therefore that the subject differegulines can be used to control or regulate the proliferation and/or differentiation of pancreatic tissue both in vivo and in vitro.

There are a wide variety of pathological cell proliferative and differentiative conditions for which the inhibitors of the present invention may provide therapeutic benefits, with the general strategy being, for example, the correction of abberrant insulin expression, or modulation of differentiation. More generally, however, the present invention relates to a method of inducing and/or maintaining a differentiated state, enhancing survival and/or affecting proliferation of pancreatic cells, by contacting the cells with the subject differegulines. For instance, it is contemplated by the invention that, in light of the apparent involvement of differegulines in the formation of ordered spatial arrangements of pancreatic tissues, the subject method could be used as part of a technique to generate and/or maintain such tissue both in vitro and in vivo. For instance, differegulines can be employed in both cell culture and therapeutic methods involving generation and maintenance β-cells and possibly also for non-pancreatic tissue, such as in controlling the development and maintenance of tissue from the digestive tract, spleen, lungs, and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. The subject inhibitors, therefore, may be used to enhance regeneration of the tissue after anti-tumor therapy. Moreover, differegulines may be useful as part of a strategy for reshaping/repairing pancreatic tissue both in vivo and in vitro. Such physiopathologies are, in particular, type II diabetes, as well as cardiovascular diseases such as, for example, hypertension and atherosclerosis. The insulin-resistance disease state in a patient may be detected conventionally via the glucose tolerance test, and the treatment according to the invention may be initiated as soon as this test proves positive, even before any clinical manifestation of an onset of disease (preventive treatment). In general, the subject method can be employed therapeutically to regulate the pancreas after physical, chemical or pathological insult. In yet another embodiment, the subject method can be applied to to cell culture techniques, and in particular, may be employed to enhance the initial generation of prosthetic pancreatic tissue devices. Manipulation of proliferation and differentiation of pancreatic tissue, for example, by a differeguline, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. Nos. 4,892,538, 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature β-cells can be observed. By utilizing the subject differegulines, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, the use of differegulines to affect tissue differentiation can be utilized as a means of maintaining graft viability.

The present method may be used to regulate regeneration of lung tissue, e.g., in the treatment of emphysema. The subject method can be used as part of a treatment of lung carcinoma and adenocarcinomas, and other proliferative disorders involving the lung epithelia.

Many other tumors may be affected by treatment with the subject compounds. Such tumors include, but are by no means limited to, basal cell carcinoma, medulloblastoma, meningioma, hemangioma, rhabdomyosarcoma, glioblastoma, sarcoma, renal carcinoma, thyroid carcinoma, bone cancer, lung cancer, chondrosarcomas, and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising differegulines can be used in the in vitro generation of skeletal tissue, such as from skeletogenic stem cells, as well as the in vivo treatment of skeletal tissue deficiencies. The present invention particularly contemplates the use of differegulines to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

The method of the present invention may be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a differeguline to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject agonists may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibro-cartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a differeguline during certain stages of the culturing process in order to manage the rate of differentiation of chondrocytes and the formation of hypertrophic chrondrocytes in the culture.

In another embodiment, the implanted device is treated with a differeguline in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. For instance, administration of a differeguline of the present invention can be employed as part of a method for regulating the rate of bone loss in a subject. For example, preparations comprising differegulines can be employed, for example, to control endochondral ossification in the formation of a "model" for ossification.

In yet another embodiment of the present invention, a differeguline can be used to regulate spermatogenesis. In a preferred embodiment, the differeguline can be used as a contraceptive. In similar fashion, differegulines of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a differeguline effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts,) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g. resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of an differeguline can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermititis refers to skin trauma resulting from allergies associated with an immune response caused by allergens such as pollens, foods, dander, insect venoms and plant toxins.

In other embodiments, antiproliferative preparations of differegulines can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing a differeguline preparation into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of corneopathies marked by corneal epithelial cell proliferation, as for example in ocular epithelial disorders such as epithelial downgrowth or squamous cell carcinomas of the ocular surface. The subject method may also be used in the treatment of proliferative diseases of retinal cells and regulate photoreceptor differentiation.

Yet another aspect of the present invention relates to the use of the subject method to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, differegulines can be used to manage hirsutism, a disorder marked by abnormal hairiness. The subject method can also provide a process for extending the duration of depilation.

The subject method can also be used in the treatment of folliculitis, such as folliculitis decalvans, folliculitis ulerythematosa reticulata or keloid folliculitis. For example, a cosmetic prepration of a differeguline can be applied topically in the treatment of pseudofolliculitis, a chronic disorder occurring most often in the submandibular region of the neck and associated with shaving, the characteristic lesions of which are erythematous papules and pustules containing buried hairs.

Regarding the in vivo modulation of lipid metabolism referred to above, apolipoprotein A-1 ("apoA1") is a major protein component of plasma high density lipoprotein (HDL) cholesterol. The circulating level of HDL in humans has been shown to be inversely correlated to the risk of atherosclerotic cardiovascular disease (ASCVD), the leading cause of morbidity and mortality in the United States, with a 3–4% increase in ASCVD for every 1% decrease in HDL cholesterol. Gordon et al., New Engl. J. Med., 321:1311 (1989). While there are currently no good therapeutic regimes that increase HDL cholesterol, it can be expected that regulating synthesis of apoAl can be utilized to affect plasma concentrations of HDL cholesterol and to decrease the risk of ASCVD. Reuben et al., Nature, 353:265 (1991).

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a differeguline, e.g., which promotes quiescense or differentiation can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative embodiment of the subject method can be used to reverse the pathological epidermal activiation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a differeguline composition in amounts sufficient to inhibit hyperproliferation of epidermal/epidermoid cells of the lesion.

Acne represents yet another dermatologic ailment which may be treated by the subject method. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercomification of the duct of a hyperactive sebaceous gland. Hypercomification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative differeguline, particularly topical preparations, may be useful for preventing the transitional features of the ducts, e.g. hypercornification, which lead to lesion formation. The subject treatment may further include, for example, antibiotics and/or antiandrogens.

The present invention also provides a method for treating various forms of dermatitis. Dermatitis is a descriptive term referring to poorly demarcated lesions which are either pruritic, erythematous, scaley, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

Ailments which may be treated by the subject method are disorders specific to non-humans, such as mange.

Thus, in another embodiment, the subject method can be used in the treatment of human cancers, particularly basal cell carcinomas and other tumors of epithelial tissues such as the skin. For example, differegulines can be employed, in the subject method, as part of a treatment for basal cell nevus syndrome (BCNS), and other other human carcinomas, adenocarcinomas, sarcomas and the like.

In one embodiment, the subject method is used as part of a treatment of prophylaxis regimen for treating (or preventing) basal cell carcinoma. The subject method can also be used to treatment patients with BCNS, e.g., to prevent BCC or other effects of the disease. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyly, syndactyly, and spina bifida. They also develop a number of tumor types in addition to BCCs: fibromas of the ovaries and heart, cysts of the skin and jaws, and in the central nervous system, medulloblastomas and meningiomas. The subject method can be used to prevent or treat such tumor types in BCNS and non-BCNS patients.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety hyperplastic or neoplastic conditions affecting platelets. In certain embodiments, pharmaceutical preparations may be non-pyrogenic, i.e., the preparation does not elevate the body temperature of the treated patient.

The differegulines for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the differeguline, its use in the pharmaceutical preparation of the invention is contemplated. Suitable vehicles and their formulation inclusive of other proteins are described, for example, in the book *Remington's*

*Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the differegulines suitable for veterinary uses, e.g., for the treatment of live stock or domestic animals, e.g., dogs.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a differeguline at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular differeguline employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

V. Pharmaceutical Compositions

While it is possible for a compound of the present invention to be administered alone, it is preferable to administer the compound as a pharmaceutical formulation (composition). The differegulines according to the invention may be formulated for administration in any convenient way for use in human or veterinary medicine.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or nonaqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject differeglines from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present differegulines may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J Pharm. Sci.* 66:1–19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra.)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as $\alpha$-, $\beta$- and $\gamma$-cyclodextrin, dimethyl-$\beta$cyclodextrin and 2-hydroxypropyl-$\beta$-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active differeguline.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the differegulines in the proper medium. Absorption enhancers can also be used to increase the flux of the differegulines across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Ore., U.S.A., 1977).

VI. Synthetic Schemes and Identification of Active Differegulines a. Combinatorial Libraries The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential differeguline lead compounds, as well as to refine the specificity, toxicity, and/or cytotoxic-kinetic profile of a lead compound.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

A variety of techniques are available in the art for generating combinatorial libraries of small organic molecules such as the subject differegulines. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject differegulines can be synthesized and screened for particular activity or property.

In an exemplary embodiment, a library of candidate differeguline diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate agonists or a substituent of a synthetic intermediate. According to the Still et al. technique, the library is synthesized on a set of beads, each bead including a set of tags identifying the particular diversomer on that bead. The bead library can then be "plated" with cells for which a differeguline is sought. The diversomers can be released from the bead, e.g. by hydrolysis.

The structures of the compounds useful in the present invention lend themselves readily to efficient synthesis. The nature of the structures, as generally described by formula I, allows the assembly of such compounds using combinatorial strategies. For example, the scheme below depicts formation of the cyclohexene core by a Robinson annulation wherein the enone is bound to a solid support. Alternatively, X or W may be used to tether the cyclohexene to the solid support. Many methods are known in the art for synthesizing polyalkenes, including condensations of phosphorous ylids (Wittig) or phosphonate anions (Horner-Emmons) with aldehydes, although many additional methods are known in the art. The strategy depicted below utilizes a thioester as an aldehyde precursor (Fukaiyama) to permit rapid, iterative extension of the polyene. An alkyllithium or other nucleophilic species, including hydride, may be added to the final polyunsaturated aldehyde in preference to the unsaturated ketone, and the resulting alcohol may then be acylated with an acid chloride or other acylating agent to afford a differeguline.

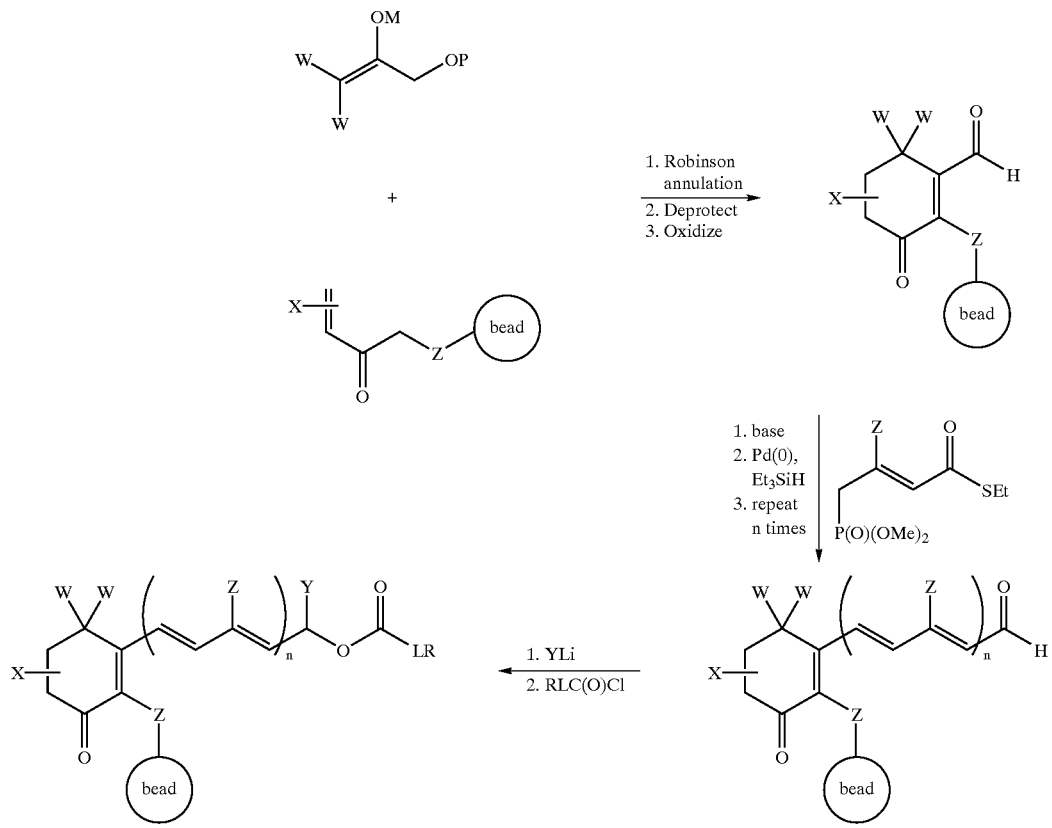

Many variations on the above and related pathways permit the synthesis of widely diverse libraries of compounds which may be tested as differegulines.

b. Screening Assays

There are a variety of assays available for determining the ability of a compound to inhibit cell proliferation or promote cell differentiation, many of which can be disposed in high-throughput formats. In many drug screening programs which test libraries of compounds and natural extracts, high throughput assays are desirable in order to maximize the number of compounds surveyed in a given period of time. Thus, libraries of synthetic and natural products can be sampled for other compounds which are differegulines.

In addition to cell-free assays, test compounds can also be tested in cell-based assays. In one embodiment, cells can be contacted with a test agent of interest, with the assay scoring for, e.g., inhibition of proliferation of the cell in the presence of the test agent.

Exemplification

The invention now being generally described, it will be more readily understood by reference to the following examples which are included merely for purposes of illustration of certain aspects and embodiments of the present invention, and are not intended to limit the invention.

EXAMPLE 1

1. General

Biliverdine was the first differeguline isolated from a living cell. It was isolated from *Xenopus laevis* oocytes and characterized as the most predominant differentiation signal in this animal. Unexpectedly, this frog oocyte compound induces terminal differentiation of a human cancer cell, HT29 colon cancer line. Therefore, biliverdine may be effective as a novel agent useful for cancer therapy. The present example, therefore, relates to 1) the purification and characterization of the physical chemical and functional properties of biliverdine from Xenopus laevis oocytes and embryos, 2) the demonstration that the biliverdine induces terminal differentiation of human colon cancer cells and can be used as an agent for the treatment of cancer, and 3) adaptations of its chemical synthesis to provide large quantities of the any of the family of bilins that may induce commitment and differentiation of embryo, stem and other undifferentiated cells.

2. Background

Summary

One differeguline, biliverdine, is formed by *Xenopus laevis* during oogenesis. This compound is stored within the oocyte in a fraction that co-elutes with yolk platelets and nuclei. It is used entirely during the period of embryo cell differentiation and organogenesis. Furthermore, UV light exposure of the ventral surface of the embryo in the first hour post-fertilization, before first cleavage has taken place, decreases the amount of biliverdine within the embryo and results in extensive teratology. Biliverdine, therefore, is essential for embryo cell differentiation. Completely unexpectedly, its biological effectiveness in driving the differentiation process forward applies to the known differentiation pathology characteristic of neoplastic adult cells. Thus, biliverdine arrests the proliferation of HT29 human colon cancer cells within 72 hours and causes overproduction of differentiation markers, such as CEA and alkaline phosphatase. The proliferative arrest extends beyond the period of exposure to the compound. Proliferation does resume 12 days later but it occurs at a slower rate (2–3 fold less) than that of control, untreated cancer cells. It is concluded that biliverdine is a differeguline with biological properties that make it a useful agent for terminal differentiation therapy of human cancer cells.

Differentiation Pathology in Neoplasia

The process of differentiation is fundamental to all biological organisms. It takes place at all stages of development from the embryo to the adult, The embryo is the product of a single cell, the egg, that is fertilized by a single sperm. The resultant embryonic cell then undergoes a series of divisions that produce many daughter cells with distinct and powerful properties. These cells are the primordial germ lines that are committed to form the three distinct categories of tissues ectodermal, mesodermal and endodermal. The differentiation of these germ lines results in the establishment of multiple tissues that organize into organs. The adult preserves some precursor, undifferentiated cells that retain the capability to form committed stem cells that terminally differentiate. These cells serve to replenish the ones that have undergone the normal aging process and died, for example in bone marrow, gonads, bowel, skin cells, and others. Periodically, therefore, these precursor cells initiate the normal process of ordered change from a primitive to a mature cell through progressive differentiation that results in the formation of a terminally differentiated white blood cell, brush border intestinal cell, etc.

The normal differentiation process of these cells can be altered for diverse reasons during carcinogenesis. Thus, exposure to radiation, chemical carcinogens, viral infections, etc., can interrupt and block the differentiation events resulting in the accumulation of partially differentiated cancer cells, as for example, in leukemia. The pathology can be localized to any level in the differentiation process resulting in histological and biochemical phenotypes characteristic of that stage.

Reversal of the Differentiation Pathology of Neoplastic Cells

Reversal of the pathology described above is a feasible objective encompassed by the term cancer differentiation therapy and reviewed in 1986 (1). The neoplastic phenotype is usually stable within an adult animal. For example, mouse teratocarcinoma, cells implanted into adult mice will maintain their malignant phenotype for hundreds of passages. However, exposure of these, and other, cancer cells to particular chemical environments, such as those found in the early embryo, can reverse the neoplastic process. Thus, when teratocarcinoma cells from a black mouse are injected into the blastula of a white mouse, a chimeric animal is formed that is composed of normal black and white cells (2). The same teratocarcinoma cells, as well as acute promyelocytic leukemia cells, can be induced to terminally differentiate by all-trans retinoic acid (3). Similarly, erythroleukemias and other forms of leukemia cells (4–10), neuroblastoma cells (11), mammary cancer cells (12) and rhabdomyosarcoma, cells (13) have been shown to differentiate by exposure to chemicals such as hexamethylenebisacetamide, dimethyl sulfoxide, retinyl methyl ether, and N,N-dimethylformamide. Metastases to the lung of embryonal carcinoma have differentiated into mature teratomas following cytotoxic chemotherapy (14). More recently, liposarcoma, colon (15–19), and breast cancer cells (20) were found to terminally differentiate when exposed to troglitazone (liposarcoma, colon and breast cancers) or butyric acid (colon cancer cells), These findings, therefore, indicate that in a suitable chemical environment, including that found in the embryo but usually not the adult, cancer cells are not stable and can be directed to differentiate into normal cells.

Molecular Processes that Regulate Differentiation

The above considerations make it apparent that the reversal of pathological conditions of differentiation that result in a progression of a cancer cell to a fully differentiated benign state is a major challenge whose achievement will be clearly aided by understanding the molecular processes that regulate as well as those that interrupt or alter differentiation itself.

Molecular messages and specific gene products are thought to participate in the differentiation processes in both the embryo and adult many of the pertinent molecules and genes have been identified. These include molecules believed to be components of the classical "organizer" (21) or to be directed by them, such as Vg1, activin, Wnt, Lim1, Gsc, Xnot HNF3, chordin, noggin, follistatin (22–28), as well as Hox, Kr, Krox20, scratch, castor, spalt, cKr2, zic, etc. (29–40). However, most of these molecules are not available in sufficient quantities, if at all, to test their capability to induce terminal differentiation of cancer cells. Moreover, many of these molecules are themselves products of other pleiotropic, master signals such as the retinoids and other hormone ligands of the nuclear receptor superfamily of proteins (41, 42). Therefore, these master switch molecules, differegulines, are the ones that act at the earliest, decisive steps in differentiation and are most likely to act on cancer cells to drive their differentiation forward. If these master chemical signals did exhibit such properties with neoplastic cells and could be obtained in large quantities, they could serve as agents useful in the area of cancer treatment.

The Oocyte as a Source of Master Bilin Switches for Differentiation: the Differegulines The oocyte is considered to be a source of these master switches. The choice of organisms for obtaining oocytes and identifying their differeguline content and metabolism are driven by a number of practical considerations. Mammalian eggs are unsuitable because they cannot be obtained in sufficient quantities, thus limiting the supply of available differegulines. Amphibian eggs are not limited in terms of quantity. Large numbers can be obtained and fertilized to obtain equally large numbers of embryos undergoing embryogenesis. Since the pertinent differegulines are present in both mammalian and nonmammalian organisms and are likely to be highly conserved through evolution, they would be the same (or very similar) in all species and could then be isolated from more accessible and available animals, tested and used with other cells. For these reasons, we selected the X. laevis oocyte/embryo system.

It requires two to three years for X. laevis to produce mature eggs capable of being fertilized (61). In marked contrast, and evidently as a direct consequence, once fertilization takes place, a tadpole with a full complement of organs derived from all three germ lines is formed in less than 3–4 days (62). This means that it takes nearly 900-fold longer to mature a single egg cell than to make an entire multicellular, multi organ tadpole. To achieve this biological feat, X. laevis oocytes must produce and store the chemical signals required for differentiation and organogenesis and use them later during the period of rapid embryogenesis. These chemical signals, acting singly or in combination, commit the single primordial fertilized oocyte cell into the three germ lines whose stem cells are subsequently directed along specific differentiation paths. Ultimately this activity results in the formation of tissues and organs. X. laevis is, thus, an excellent system; the oocytes allow us to identify and isolate these master chemical signals while the embryo itself provides the means to test their function(s).

Surprisingly, the most predominant differeguline that is formed by X. laevis during oogenesis and remains as such in both mature stage VI oocytes and embryos at different stages of development. It is the bilin biliverdine.

The bilin is compartmentalized within the oocyte. It is not in the cytosol but rather co-elutes with vesicles, yolk platelets, and nuclei when analyzed in an isopycnic sucrose gradient. This finding provided unexpected insight into a long-held mystery, namely, the basis for the teratology that results when the vegetal hemisphere of the X. laevis embryo is exposed to UV light before the first cleavage, and the explanation for the rescue from teratology by temporary orientation of the exposed embryo 90° from the vertical axis (63, 64). Since the bilin is contained within yolk platelets and other granules, such as, for example, germinal granules, and those structures settle to the vegetal pole during this period, their chemical contents could become accessible to UV radiation. We have exposed embryos to UV irradiation (358 nm) and found that about 10% of the bilin is destroyed, providing initial support for the proposition (see Detailed Description, below).

The Oocyte Bilin Exhibits Biological Activity with Human Cancer Cells

Further evidence in support for the assignment of biliverdine as a master chemical differentiation switch is the demonstration that it induces differentiation of HT 29 colon cancer cells cultured under in vitro conditions (see Detailed Description, below). The differentiation activity is achieved by incubating the cells with biliverdine as purified. The initial effect is an arrest of cellular proliferation within the first three days of exposure. The arrest persists for the entire exposure period and for about 12 days following removal of the biliverdine. The early phase of the arrest; is accompanied by over expression of the differentiation markers, CEA, and alkaline phosphatase. Once cell division resumes, the rate is about 2.3 times slower than for the control.

Models for Studying the Capability of Master Chemical Switches to Induce Terminal Differentiation of Cancer Cells in vivo The translation of in vitro observations to in vivo conditions is greatly facilitated by a number of animal models that are currently in use to evaluate the efficacy of agents in the treatment of cancer. Some use animals that are immunodeficient (athymic) and others, ones with a fully functional immune system. The former allows for xenogeneic and syngeneic tumors to be grown and tested while the latter are best for syngeneic tumors grown under conditions where the animal's immunological system participates in the response to therapy (65–67). Since the issue of pertinence here is the capability of biliverdine and its derivatives to induce terminal differentiation of human tumors of various origins, the initial model of choice would be the athyrnic mouse model for which there is experience in growing tumors as either primary subcutaneous tumors (65) or as metastatic models (68–70). In the former case, the H29 human colon cancer cell line has been used extensively while for the latter there are now several established models with other human colon and prostate cancer cells. These can be tested with biliverdine for responsiveness to terminal differentiation in vivo.

Conclusion

The finding that biliverdine is the predominant differeguline species of a major living form and that it has broad biological effects on differentiation of both frog cells and colon cancer cells strongly argues that it is the natural ligand for these receptors. As the natural ligand, it should facilitate achieving the objective of inducing terminal differentiation, perhaps at lower concentrations and, therefore, facilitate its application in humans by virtue of reduced toxicity. It also directs the design of other related molecules for targeted differentiation therapy.

Biliverdine has properties that identify it as a master differeguline. Specifically, it is used during embryogenesis, and its destruction or change in molecular structure by exposure to UV light (358 nm) results in major teratology. Unexpectedly, biliverdine induces differentiation of HT29 human colon cancer cells. The results indicate that differegulines have a broad application to biological processes, since they can induce differentiation not just of embryonic but also of non embryonic cells, including human cancer cells.

Citations

1. Pierce B G, Speers W C, Tumors as Caricatures of the Process of Tissue Renewal: Prospects for Therapy by Directing Differentiation. Cancer Res. 48:1996–2004, 1988.
2. Mintz B, Ilmensee J D, Normal Genetically Mosaic Mice Produced from Malignant Teratocarcinoma. Cells. Proc. Natl. Acad Sci. USA 72:3585–3589,1975.
3. Strickland S, Mahdavi V, The Induction of Differentiation in Teratocarcinoma stem cells by retinoic acid. Cell 15:393–403, 1978.
4. Tanaka M., Levy J, Terada M, Breslow R, Rifkind R A, Marks P A, Induction of Erythroid Differentiation in Murine Virus Infected Erythroleukemia Cells by Highly Polar Compounds. Proc. Natl. Acad Sci. USA 72:1002–1006, 1975.
5. Fibach E, Reuben R C, Rifkind R A, Marks P A. Effect of Hexamethylene bis acetarnide on the Commitment to Differentiation of murine erythro cells. Cancer Res. 37:440–444, 1977.
6. Friend C, Scher W, Holland J G, Sato T, Hemoglobin Synthesis in Murine Virus Induced Leukemia Cells in vitro Stimulation of Erythroid Differentiation by Dimethyl Sulfoxide. Proc. Natl. Acad. Sci. USA 69:378–382, 1971.
7. Huberman, E, Collaham, W, Induction of Terminal Differentiation in Human Promyelocytic Leukemia Cells by Tumor Promoting Agents, Proc. Natl. Acad. Sci. USA 76:1293–1297, 1971.
8. Collins S J, Ruscetti J W, Gallagher R E, Gallo R C. Terminal Differentiation of Human Promyelocytic Leukemia Cells Induced by Dimethyl sulfoxide and other Polar Compounds, Proc. Natl. Acad. Sci. USA 75:2458–2462, 1978.
9. Marks P A, Sheffrey K, Rifkind R A, Induction of Transformed Cells to Terminal Differentiation and the Modulation of Gene Expression. Cancer Res. 47:659–666, 1987.

10. Feakon E R, Phillip B A, Burke J, Schiffer C A, Zehnbauek B A, Vogelstein B, Differentiation of Leukemia Cells to polymorphonuclear Leukocytes in Patients with Acute Nonlymphocytic Leukemia. *N. Eng. J. Med.* 315:15–24, 1986, 11. Schubert D S, Humphreys S, DeVitry F, Jacob F, Induced Differentiation of Neuroblastoma. *Dev. Biol.* 25:514–546, 1971, 12. Grubbs C J, Moon R C, Spom M B, Newton D L, Inhibition of Mammary Cancer by Retinyl Methyl Ether. *Cancer Res.* 37:599–602, 1977, 13. Dexter D L, NN-Dimethylformamide-induced Morphological Differentiation and Reduction of Tumorgenicity in Cultured Mouse Rhabdomyosarcoma Cells. *Cancer Res.* 37:3136–1140) 1977.

14. Carr B I, Gilchrist K W, Carbone P P, The Variable Transformation in Metastases from Testicular Germ Cell Tumors: The Need for Selective Biopsy. *J. Urol.* 126:52–54, 1981.

15. Tontonoz P, Singer, S, Forman, B K, Sarraf P, Fletcher, J A, Fletcher, C D M, Brun, F P, Mueller, E, Altiok, S, Oppenheim, H Evans, R M and Spiegelman, B M. Terminal Differentiation of Human Liposcarcoma Cells Induced by Ligands for Peroxisome Prolifertor-activated Receptor and the Retinoid X receptor. *Proc. Natl. Acad, Sci. USA* 94:237–241, 1997.

16. Schwartz B, Carmel A-G, Sylvie P C, Sodium Butyrate Induces Retinoblastoma Protein Dephosphorylation, p16 Expression and Growth Arrest of Colon Cancer Cells. *Mol Cell Biochem.* 188:21–301, 1993.

17. Sarref P, Mueller E, Jones D, King F J, DeAngelo D J, Partridge J B, Holden S A, Chen I. B, Singer S, Fletcher C, Spiegelman B. Differentiation and Reversal of Malignant Changes in Colon Cancer through PFARgama. *Nature Medicine* 4:1046–1052. 1998.

18. Gum J R, Kam Wk, Byrd J C, Hicks J W, Sleisinger M H, Kim Y S, Effect of Sodium Butyrate on Human Colonic Adenocarcinoma Cells Industion of Placental-like Alkaline Phosphatase. *J. Biol. Chem.* 262:1092–1097, 1987.

19. Garnet L, Daviaud D, Denis-Pouxviel C, Remesy C, Murat J C, Effects of Short-chain Fatty Acids on Growth and Differentiation of the Human colon-cancer cell line HT29. *Int. J. Cancer* 52:286–289, 1992.

20. Mueller E, Sarrat P, Tontonoz P, Evans R M, Martin K J, Zhang M, Fletcher C, Singer S, Spiegelman B K, Terminal Differentiation of Human Breast Cancer through PPAR. *Mol. Cell* 1:465–470,1998.

21. Spemann H, Mangold H, Induction of Embryonic Primordia by Implantation of Organizers from a Different Species. In B. R Willier and J. M. Oppenheimer (eds.), Foundations of Experimental Embryology. Hafner, New York, pp. 144–194, 1924.

22. Smith W C, Harland R M, Expression Cloning of Noggin, a New Dorsalizing Factor Localized to the Spemann Organizer in Xenopus Embryos. *Cell* 70:829–840, 1992.

23. Hemmati-Brivanlou A, Kelly O G, Melton D A, Follistatin, an Antagonist of Activin, is Expressed in the Spemarin Organizer and Displays Direct Neuralizing Activity. *Cell* 77:283–295,1994.

24. Sasai Y, Lu B, Steinbrisser H, Geissert D, Gont L K, De Robertis E M, Xenopus Chordin: A Novel Dorsalizing Factor Activated by Organizer-specific Homeobox Genes. *Cell* 79:779–790,1994.

25. Takada S, Stark K L, Shea M J, Vassileva G, McMahon J A, McMahon A P, Wnt-3a Regulates Somite and Tailbud Formation in the Mouse Embryo. *Genes Dev* 8:174–189, 1994.

26. Ang S L, Rossant J, *HNF-3 beta is Essentialfor Node and Notochord Formation in Mouse Development.* Cell 79:561–574, 1994.

27. Weinstein D C, Ruiz I A A, Chen W S, Hoodless P, Prezioso V R, Jessell T M, Darnell J E, The Winged-heliz Transcription Factor HNF-3 beta is Required for Notochord Development in the Mouse Embryo. *Cell* 78:575–588, 1994.

28. Dawid J B, Intercellular Signaling and Gene Regulation during Early Embryogenesis of Xenopus Laevis. *J. Biol. Chem.* 269:625 9–6262, 1994.

29. Roark M, Sturtevant M A, Emery J, Vaessin H, Grell E, Bier E, Scratch, a panneural Gene Encoding a Zinc Finger Protein related to Snail, Promotes Neuronal Development. *Genes Dev.* 9:2384–2390,1995.

30. Mellerick D M, Kassis J A, Zhang S D, Odenwald W F, Castor Encodes a Novel Zinc Finger Protein Required for the Development of a subset of CNS Neurons in Drosopliila. *Neuron* 9:799–903, 1992.

31. Kuhnlein R P, Frommer G, Friendrich M, Gonzalez-Gaitan M, Weber A, Wagner-Bemholz J F, Gehring W J, Jackle H, Schuh P, Spalt Encodes an Evolutionarily conserved Zinc Finger Protein of Novel Structure which Provides Homeotic Gene Function in the Head and Tail Region of the Drosophila Embryo. *EMMO J.* 13:168–179, 1994.

32. Swiatek P J, Gridley T, Perinatal Lethality and Defects in Hindbrain Development in Mice Homozygous for a Targeted Mutation of the Zinc Finger Gene Krox2o, *Genes Dev.* 7:2071–2084, 1993.

33. Bernard O, Ganiatsas S, Kannourakis G, Dringen R, Kiz-1, a Protein with LIM Zinc Finger and Kinase Domains, is Expressed Mainly in Neurons. *Cell Growth Differ.* 5:1159–1171,1994.

34. Schutz B, Niessing J, Cloning and Structure of a Chicken Zinc Finger cDNA: restricted Expression in Developing Neural Crest Cells, *Gene* 148:227–236, 1994.

35. Nagai T, Aruga J, Takada S, Gunther T, Sporle It, Schughart K, Mikoshiba K, The Expression of the Mouse Zic1, Zic2, and Zic3 Gene Suggests an Essential Role for Zic Genes in Body Pattern Formation. *Dev Biol.* 182:299–313, 1997.

36. Kostich W A, Sanes J R, Expression of zfh-4 a new Member of the Zinc Finger-homeodomain Family, in Developing Brain and Muscle. *Dev. Biol.* 202:145–152, 1995.

37. Mevel-Ninio M, Terracol R, Kafatos F C, The Ovo Gene of Drosphilia Encodes a Zinc Finger Protein Required for Female Germ Line Development. *EMBO J* 10:2259–2266, 1991.

38. Redeman N, Gaul U, Jackle H, Disruption of a Putative Cys-zinc Interaction Eliminates the Biological Activity of the Kruppel Finger Protein. *Nature London* 332:90–92, 1988.

39. Perrotti D, Melotti P, Skorski T, Casella I, Peschle C, Calabretta B. Overexpression of the Zinc Finger protein MZF1 Inhibits Hematopoietic Development from Embryonic Stem Cells: Correlation with Negative Regulation of CD34 and c-rnyb Promoter Activity. *Mol. Cell Biol.* 15:6075–6097, 1995.

40. Krishnaraju K, Nguyen H Q, Liebermann D A, Hoffman B, The Zinc Finger Transcription Factor Egr- I Potentiates Macrophage Differentiation of Hematopoietic Cells. *Mol. Cell Biol.* 15:5499–507, 1995.

41. Leid M, Kastner P, Chambon P, Multiplicity Generates Diversity in the Retinoic Acid Signaling Pathways, *TIBS:*427–433, 1992.

42. Pfhal, M, Retinoids: Concepts for Separation of Desirable and Undesirable Effects in the Treatment or Prevention of Cancer. In: Hormones and Cancer. Ed. M V Vederlds, birkhauser, Boston. pp. 127–146, 1996.
43. Thaller C, Eichele G, Identification and Spatial Distribution of Retinoids in the Developing Chick Limb Bud, *Nature* 327:625–628, 1987.
44. Eichele G, Retinoids and Vertebrate Limb Pattern Formation. *Trends Genet* 5:246251, 1989.
45. Broches J P, Retinoic Acid and Limb Regeneration. *J. Cell Sci. Suppl.* 13:191–198, 1990,
46. Broches J P, Retinoids, Homeobox Genes and Limb Morphogenesis. *Neuron* 2:1285–94.
47. Durston A J, Timmermans J P, Hage W J, Hendricks H F, de Vries N J, Heideveld M, Nieuwkoop P D, Retinoic Acid Causes an Anteroposterior Transformation in the Developing Central Nervous System. *Nature* 340:140–144, 1989,
48. Sive H L, Draper B W, Harland R M, Weintraub H, Identification of a Retionic AcidSensitive Period During Primary Axis Formation in *Xenopus Laevis*. *Gene Dev.* 205:41–45, 1990,
49. Creech K J, Kimelman D, Juchau M R, Xenopus laevis: A Model System for the Study of Embryonic Retinoid Metabolism. II. Embryonic Metabolism of all-trans-3,4-didehydroretinal to all-trans-3,4-didehydroretinole Acid. *Drug Metab. Dispos.* 23:83–89, 1995.
50. Costaridis P, Horton C, Zeitlinger J, Holder N, Maden M, Endogenous Retinoids in the Zebrafish Embryo and Adult. *Develop. Dynm.* 1996.
51. Pijnappel W W M, Hendriks H F, Folkers G E, van den Brink C E, Dekker E J, Edelenbosch C, van der Saag P T, Durston A J, The Retinoid Ligand 4-oxo-retinoic Acid is a Highly Active Modulator of Positional Specification. *Nature* 366:340–344, 1993.
52, Thaler, C. and Eichele, G. Isolation of 3,4-didehydroretinoic acid, a novel morphogenic signal in the chick wing bud. *Nature* (London), 345:815–819, 1990.
53. Blumberg B, Bolado J, Derguini F, Craig A J, Moreno T A, Chakravarti D, Heyman R A, Buck J, Evans R M, Novel Retinoic Acid Receptor Ligands in Xenopus Embryos. *Proc. Natl. Acad. Sci., USA* 93:4873–4878, 1996.
54. Achkar C C, Derguini F, Blumberg B, Langston A, Levin A A, Speck J, Evans R M, Bolado J, Nakanishi K, Buck J, Gudas L J, 4-oxoREtinol, a New Natural Ligand and Transactivator of the Retinoic Acid Receptors. *Proc. Natl. Acad. Sci., USA* 93:48794884, 1996.
55. Azuma, m, Seki, T, and Fujishita, S. Changes in egg retinoids during development of Xenopus laevis. *Vision Res.* 30(10):1395–1400,1990.
56. Kraft J C, Juchau M R, Correlations between conceptual concentrations of All-trans-retinoic Acid and Dysmorphogenesis after Microinjections of all-trans-retinoic Acid, 13-cis-retinoic acid, all-trans-retinoyl-glucuronide, or Retinol in cultured Whole Rat Embryos, *Drug Metab. Dispos.* 20:218–224,1992.
57. Zucos H M, Evans R Ma, Retinoic Acid and Retinoic Acid Receptors in Development. *Mol. Neurobiol.* 10:169–84, 1995.
58. Chambon, P. A Decade of Molecular Biology of Retinoic Acid Receptors. *FASEB J.* 10:940–954.
59. Mendelsohn G, Lohnes D, Decimo D, Lufkin T, LeMeur M, Chambon P, Mark M, Function of the Retinoic Acid Receptors (RARs) During Development (II) Multiple Abnormalities at Various Stages of Organogenesis in RAR Double Mutants. *Development* 120:2749–2771.
60. Gronemeyer R and Landet V. (1996) Transcription Factors: Nuclear Receptors. Protein Profile vol. 2. Academic Press, New York.
61. Grant P, Phosphate Metabolism during Oogenesis in *Rana temporaria*. *J. Exp. Zool.* 124:513–543, 1953.
62. Nieuwkoop, P D and Faber, J. Normal Table of Xenopus laevis (Daudin). 2nd edition. Amsterdam: North Holland Publ.Co. 1967
63. Scharf S R, Gerhart J C, Determination of the Dorsal-Ventral Axis in Eggs of *Xenopus laevis*: Complete Rescue of uv-Impaired Eggs and Oblique Orientation before First Cleavage. *Develop. Biol.* 79:181–198, 1980.
64. Wakahara M, Partial Characterization of 'Primordial Germ Cell-forming Activity' Localized in Vegetal Pole Cytoplasm in Anuran Eggs. *J. Embryol. Exp. Morph.* 39:21–233, 1977.
65. Olson Y A, French T C, Vallee B U Fett J W, A Monoclonal Antibody to Human Antiogenin Suppresses Tumor Growth in Athymic Nee. Cancer Research 54, 45764579,1994.
66. Donehower L A, Harvey K Stage B L, McArthur M J, Montgomery C- Jr., Butel J S, Bradley A, Nee Deficient for p53 are Developmentally Normal but Susceptible to Spontaneous Tumors. Nature 356:215–221, 1992
67. Donchower L A, The p53-deficient Mouse: A Model for Basic and Applied Cancer Studies. Semim. Cancer Biol 7:269–278, 1996,
68. Preflow T, Dehnoro C, Dilley G, Spadafora C, Preflow T, Transplantation of Human Prostatic Carcinoma into Nude Mice in Matrigel. *CancerRes* 51:3814–3817,1991.
69. Morikawa & Walker S K Nakajima K Pathak S, Jessup Y K Fidler I J, Influence of Organ Environment on the Growth, Selection, and Metastasis of Human Colon Carcinoma Cells in Nude Mice. Cancer Res. 48, 6863–6871, 1988.
70. Stephenson R A, Dinney C P N, Gohji Y., Ordonez N G, Yjllion J J, Fidler 11, Metastatic Models in Human Prostate Cancer using Orthotopic Implantation in Nude Mice. *J. Cancer Inst.* 94:951–957,1992,
71. Formelli F, Cleris L, Synthetic Xetinoid Fenretinide is Effective Against a Human Ovarian Carcinoma Xenograft and Potentiates Cisplantin Activity, *Cancer Res.* 51:5374–5376, 1993.
72. Bischoff E D, Boehm W, Nadzan A M, Heyman R A, Shalinsky 1DR, AIRTI 550, A Potent RAR-selective Refinoid, Dose-dependently Inhibits the Growth of Established Squamous Cell Carcinoma Xenografts in Athymic Nude Mice. Proc. Anna. Meet. *Am. Assoc. Cancer Res.* 37:A1576,
73. McCarthy D I, Dollar G R, Hill D L Toxicity and Atitumor Activity of Liposome-entrapped Retinoid Rol.3–7410, Sel. *Cancer Ther.* 7:151–157,1991.
74. Shalinsky D R, Bischoff Ed, Lamph W W, Zhang L, Boehm M F, Davies P J, Nadzan Am, Heyman R A, A Novel Retinoic acid Receptor-selective Retinoid, ALRT 15 50, has Potent Antitumor Activity Against Human Oral Squamous Carcinoma Xenografts in *Nude Mice—Cancer Res,* 57; 162–168, 1997.
75. Schleicher, R I Moon, R C, Patel, M& Beattie, C W. Influence of retinoids on growth and metastasis, of melanonia in atbymic xx&e. Ceawer Res. 48(6): 1465–1469, 1988.
76. Nomizu T, Falchuk W Vallee B L. Zinc, Iron and Copper Content of *X. laevis* oocyte and Embryos. Mol. *Reprod Develop,* 1:314–319, 1993.
77. Nieuwkoop, P D and Faber, 1. Normal Table of *Aenopus laevis* (Daudin). 2nd editionAmsterdam: North Holland Publ. Co. 1967, 78. Jomvall. K Falchuk, K K Geract G, Vallee, B L, 1, 10-phenanthroline and *Xenopus laevis* Teratology—*Biochem Res. Commun.* 200:1407–1413, 1994,
79. Scharf, S(R+1 and Gerhart, J C. Axis Determination in Eggs of *Xenopus laevis*: a Critical Period before First Cleavage, Identified by the Common Effects of Cold, Pressure and Ultraviolet Light. Dev. Biol- 99; 75–87, 1983.
80. Holwill, S, Heasman, J., Crawley, C R and Wyle, C C. Axis and Germ Line Deficiencies caused by UV Irradiation of Xenopus oocytes cultured in vivo. *Development.* 100:735–743, 1987.
81. Wall D A, Paid S- The intracellula fate of vitellogenin in Xwopus oocytes is determined by its extracellular concentration during endocytoses. *J Biol. Chen* 262:14779–14789, 1987.
82. Wall D A, Meleks 1. AN unusual lysosomal compartment involved in vitellogenin endocytosis by Xenopus oocytes. J Cell Biol 101:1651–1664, 1985.
83. Falchuk K H Montorzi M, Vallee B L, Zinc Uptake and Distribution in *Xenopus laevis* Oocytes and Embryos. *Biochemistry* 34:16524–16531, 1995.
84. Hausen, P and Riebesell, M. The Eady Development of *Xenopus Laeva*. Springer-Verlag, Berlin Heidelberg New York. Plates 7–10. 1991.
85. Scharf S(R+1, Gerhart J C. Determination of the Dorsal-Ventral Axis in Eggs of *Xenopu laevis*: Complete Rescue of uv-Impaired Eggs and Oblique Orientation before First Cleavage. Develop. Biol. 79; 181–199,1980.
86. Wakahara, M. Partial Characterization of 'Primordial Germ Cell-forming Activity' Localized in Vegetal Pole Cytoplasm in Anuran Eggs. *J Entbryol Exp. Morph.* 39; 221 233,1977.
87. Sumastis J D, U.S. Pat. No. 3,311,656, Mar. 28,1967, Chem, Abstr. 67:22052-d.
88. Waldmann D, Thorsten & Schreier P, Iron O W Porphinate/H202-Mediated Conversion of All-(F-)-Retinol. Z Naturforch 50b. 589–594,1995.

Detailed Description

Sources of Bilins

A stock solution of modified Steimberg's buffer (5.8 mM NaCl, 0.67 mM KC1, 0.4 mM $MgSO_4$, 3.4 mM $CaCl_2$, 4.6 mM Tris, 6 mM $HNO_3$, pH 7.4) was prepared with compounds of highest purity, diluted and used as described below. Oocytes at different stages of maturation were obtained from 6–7 cm long female *X. laevis* frogs. Frogs were anesthetized by immersion in 0.1% p-aminobenzoic acid ethyl ester, 0.3% $KHCO_3$, pH 7.5. The abdominal cavity was opened using sterile conditions to remove the ovarian lobes. The fibrous sheath of the ovarian lobes was removed by treatment with 0.57% collagenase for 45 minutes at 37° C. Oocytes at each stage of maturation were collected by first separating smaller stages 1–4 from larger stages 5 and 6 eggs by filtering the total oocyte suspension through a size 30 mesh screen placed in a glass funnel. The screen was fixed at a position 15 cm above the bottom in a glass beaker totally immersed in 20% Steimberg buffer. The eggs were poured into the funnel. Stages 1–4 passed through the screen while stage 5 and 6 remained on the screen. Stages 3, 4, 5, and 6 then were separated on the basis of their size and morphology using Dumont's criteria (20). The separated oocytes were weighed, snap frozen in liquid nitrogen, and stored at −80° C.

Embryos were obtained by in vitro fertilization techniques (76). Fifty units of pregnant mare's serum were injected into the dorsal lymph sac of 6–7 cm female *Xenopus laevis* frogs. 92 hours later, 500 U human chorionic gonadotropin (hCG) were administered again into the dorsal lymph sac. Within 12–14 hours a given frog produced greater than 1000 eggs that were fertilized in vitro. Frog testes were placed in 60×15 mm dishes containing 80% Steimberg's solution, and macerated to prepare a sperm solution. Viability was confirmed by observing motility using a light microscope. The female was induced to shed eggs by massage of the abdomen and the area above the cloacal valves. For fertilization, eggs were deposited directly into the sperm solution. Once this was achieved, all embryos were dejelled using a 2% L-cysteine solution, pH 8.0. The embryos remained in this solution for 5 minutes and were then washed 5× in 20% Steimberg's solution. Embryos were then transferred to 150×25 mm dishes containing 20% Steimberg's solution. The solution was changed daily for the first week after which the embryos were placed in a 10 gallon tank containing aerated Milli-Q water. Progression of embryonic development was scored by light microscopic observation of gross morphological changes according to Nieuwkoop and Faber (77). Once the embryos reached the desired stage of maturation they were counted, snap frozen in liquid nitrogen, and stored at −80° C.

Approximately 1000 control, unfertilized eggs were shed directly into plastic dishes containing only 20% Steimberg's solution but no sperm. These were dejelled as above, counted, and snap frozen in liquid nitrogen. Eggs from 6–7 cm albino female frogs were similarly collected.

Bilin Extraction

All procedures involving oocyte manipulation, gradient loading, fraction collection and lipid extraction were carried out under subdued amber light or covered in aluminum foil when not possible. Exposure to oxygen and heat was minimized by keeping all samples covered and on ice.

Oocytes at each stage of maturation and embryos at different development points were removed from storage, allowed to thaw, and the one vol. of ice cold stabilizing buffer (5 mg/ml ascorbic acid, 5 mg/ml EDTA in PBS, pH 7.3) was added. Some oocyte and all embryo samples were used for identification of bilins and subsequent purification. These were sonicated maintaining the sample on ice using a VWR Branson Sonifer 450. The duty cycle was set to 40% and the output control was set to 4.5. The samples were sonicated 3× in 15 sec. intervals. Two vol. of extraction buffer (ethyl acetate/methyl acetate 8/1 plus 50 µg/ml butylated hydroxytoluene) were added to the sonicates. The samples then were placed on a rotator for 20 minutes in the cold room, centrifuged at 1000×g for 10 min. and the organic layer removed and stored on ice. The procedure was repeated and resultant organic layers were pooled. The samples were dried by exposure to a stream of nitrogen in the dark. The dried material was resuspended in 160 µl methanol an stored at −80° C.

Intracellular Localization of Bilins by Isopycnic Fractionation of Homogenized *Xenopus laevis* Stage VI eggs Oocytes were homogenized, instead of undergoing sonication, and then fractionated in an isopycnic sucrose gradient as described below. For these experiments, approximately 250 stage VI eggs were used. These oocytes were treated identically as above but the initial stabilizing buffer was first decanted, new buffer added to a final volume of 1.2 ml and then homogenization was carried out manually and gently keeping samples on ice. A stepwise sucrose gradient was prepared with 1 ml layers composed of EDTA 30 mM, butylated OH toluene 0.5 mg/ml (5 µL/ml from a stock solution of 100 mg/ml in methanol), and sucrose in amounts enough for the fluid to reach the targeted specific gravity. The density of the layers were from the bottom to the top of the tube (in g/ml): 1.26, 1.24, 1.23, 1.22, 1.21, 1.20, 1.18, 1.16, 1.12, 1.08. The gradient was kept at 0° C. One milliliter of the homogenate was carefully loaded on top of the gradient without disturbing the layers. The preparation was spun with an SW40 rotor (Beckman) at 25,000 rpm, 0° C., for 22 hours. Afterwards, eight equal fractions of 1.375 ml were manually collected from the top of the gradient by means of a glass capillary tube and a peristaltic pump. Upon collection, the fractions were immediately blast frozen by submersion in liquid nitrogen and then stored at −80° C. for further processing. The bilins and retinoids in each gradient layer were extracted as described above.

Separation of Bilins and Retinoids by Chromatography

The bilins and retinoids in the oocyte and embryo extracts were separated using HPLC chromatography. Two different systems were used with the same Jupiter 5 $\mu$C 18 300A 250×4.6 column (Phenomenex). The first system used consisted of a Water Model 6000A solvent delivery system, Waters Model 440 absorbance reader, and a Waters automated gradient controller. A number of gradients profiles were used in this system. In all cases, the initial buffer (A) consisted of 10% acetonitrile, ammonium acetate 0.231 g/l, pH 6.5 while final concentration of buffer (B) was 100% acetonitrile. The time to arrive at 100% Buffer B was set to maximize the purification of the bilins and retinoids. Initially, the time was 60 minutes. Subsequently, to optimize isolation of the major bilin and retinoid species in the samples, another gradient profile was used consisting of from 10 to 28% in 12 minutes, then to 68% in 60 min and up to 100% in 62 min. The Waters Maxima 820 software was used to analyze the chromatogram. The samples injected first were vortexed for 1 min. and centrifuged at 1000×g for 2 min. The supernatant was injected into the HPLC. All-trans-retinol, all-trans-retinal, 13-cis-retinoic acid, 9-cis-retinoic acid, and all-trans-retinoic acid were obtained from Sigma. These standards were dissolved in methanol to a concentration of $3.3 \times 10^{-4}$ M. 25–100 $\mu$l of each standard solution was injected into the HPLC instrument. Fractions were collected at one min. intervals.

The second system, used to analyze the extracts from the sucrose gradient fractions, was an Alliance chromatography station (Waters) equipped with an automatic injector, in line vacuum pump, and a diode array detector. The data was collected and processed with a Millenium software (Millipore). Buffer A was composed of ammonium acetate 20 mM, pH 4.6. Buffer B was acetonitrile 100%. It was used for chromatographic separation of the bilins and retinoids obtained by the isopycnic sucrose gradient fractionation. Samples applied were dissolved in 240 $\mu$L of methanol. 100 $\mu$L of each solution were loaded to the column. The elution was carried out with the following gradient; 0 to 100% buffer B lineal increase in 45 min, 100% buffer B for 15 min, solvent flow 1 ml per minute, temperature 22° C. The eluate was monitored at 340 nm.

Storage and Handling of Bilins

The eluted fractions were collected in the dark by encasing the fraction collector in an aluminum foil covered box to prevent exposure to the light. The fractions were dried under a stream of nitrogen and stored at −80° C. After 25 individual fractions of the major bilin peak were collected and dried they were pooled in 3 ml of 100% ethanol. The material was stored as above in 40 $\mu$l aliquots. Before submitting samples for analyses, all were checked by rechromatography on HPLC to insure they had not broken down or isomerized.

Fraction Analyses

Selected fractions were identified by their retention times corresponding to those of known standards. Unknown peaks were first analyzed on the basis of the absorption spectra using a Varian Cary UV/Visible Spectrophotometer. The samples were scanned from 250 nm to 900 nm. Fractions were further analyzed by mass spectroscopy. Eight fractions of the major bilin peak were pooled and dried under nitrogen gas. The dried sample was prepared at a concentration of approximately 5 ng/$\mu$l using a buffer of 75:25 acetonitrile-:water containing 1 nm ammonium acetate. Samples were analyzed in positive ion mode on the Finnigan LCQ ion trap mass spectrometer, using atmospheric pressure chemical ionization. The sample was also analyzed by IR.

UV Irradiation of Pre-cleavage Embryos

The effects of UV irradiation on the bilin content of $X$. laevis embryos were studied. Stage VI pigmented eggs were obtained and fertilized as described above. Immediately after fertilization the single-celled embryos were divided into two batches, control and exposed to a source of light emitting at 358 nm. The experimental embryos (approximately 200 per batch) were placed on top of a quartz base filled with 20% Steinberg buffer and exposed from below to 358 nm radiation for 10 min, prior to the first cleavage and all during 0.2 to 0.6 of the first cycle.

After UV irradiation, a set of embryos from each group were collected, dejellied with 2% L-cysteine, 0.16M NaOH and washed extensively in 20% Steinberg's buffer. The embryos then were transferred to a 15 mL test tube filled with stabilizing buffer (PBS, Ascorbic acid 5 mg/mL, EDTA 5 mg/mL, pH 7.3 0° C.) and allowed to settle. The remaining buffer was removed and new stabilizing buffer was added to a final volume of 2 mL. The bilins and retinoids in each batch were extracted, separated and analyzed as described. Another set of embryos were allowed to develop until stages 35–40. The gross morphological appearance of each individual embryo was evaluated by light microscopy as previously described (78). The developmental teratology characteristic of the "UV syndrome," was scored by standard criteria and categorized into the five groups comprising the "index of axis deficiency" (79,80). Briefly, the published criteria used (80) include a grade of [0] for normal morphology. Index of deficiencies I–V were assigned for [I] microcephalic with reduced size of eyes' [II] microcephalic with fused eyes or cyclopia with some retinal pigment visible; [III] extremely microcephalic, no or minimally visible retinal pigment, at least one otic vesicle present; [IV] acephalic but intact somites identified; [V] no neural or mesodermal structures present.

Cell Culture Conditions

Human HT 29 colon cancer cells were purchased form the American Type Culture Collection. Cells were maintained in Dulbecco's Modified Eagle's Medium (DME) supplemented with 5% heat-inactivated fetal bovine serum, 2 mM glutamine, and antibiotics (DME/5%). All cell lines were incubated in a humidified 5% $CO_2$/air environment. They were maintained at 37° C. in 5% $CO_2$ covered in aluminum foil to prevent exposure to the light. A total of $1 \times 10^6$ cells were incubated per flask and allowed to attach overnight. Media was changed every third day. Cell counts were performed on a Coulter Counter following detachment of cells by standard trypsinization procedures. Only those preparation exhibiting cell viability greater than 95% were used. The cells were incubated with 0.4 $\mu$M biliverdine, a concentration that did not induce apoptosis but arrested cell proliferation, as described below. The period of exposure was followed by incubation in the absence of biliverdine. Cell numbers were monitored until proliferation resumed. The production of CEA and alkaline phosphatase was measured as described below.

Results

Oocycte Bilins

The most prominent fraction of the chromatographic profile is less hydrophobic than the retinoids and, therefore, elutes earlier at 17 min with 44.7% acetonitrile. This retention time does not correspond to β-carotene, retinol, retinal, 13-cis retinoic acid, 9-cis retinoic acid, or all-trans retinoic acid. On a quantitative basis, this fraction represents more than 50% of the total retinoid pool, about 20–30 μg compound per ovary. The recovery of this bilin is dependent on the presence of the chelating agent EDTA in the stabilization buffer used prior to homogenization or sonication. In its absence, the amounts recovered are variable and always reduced.

Figure 2:
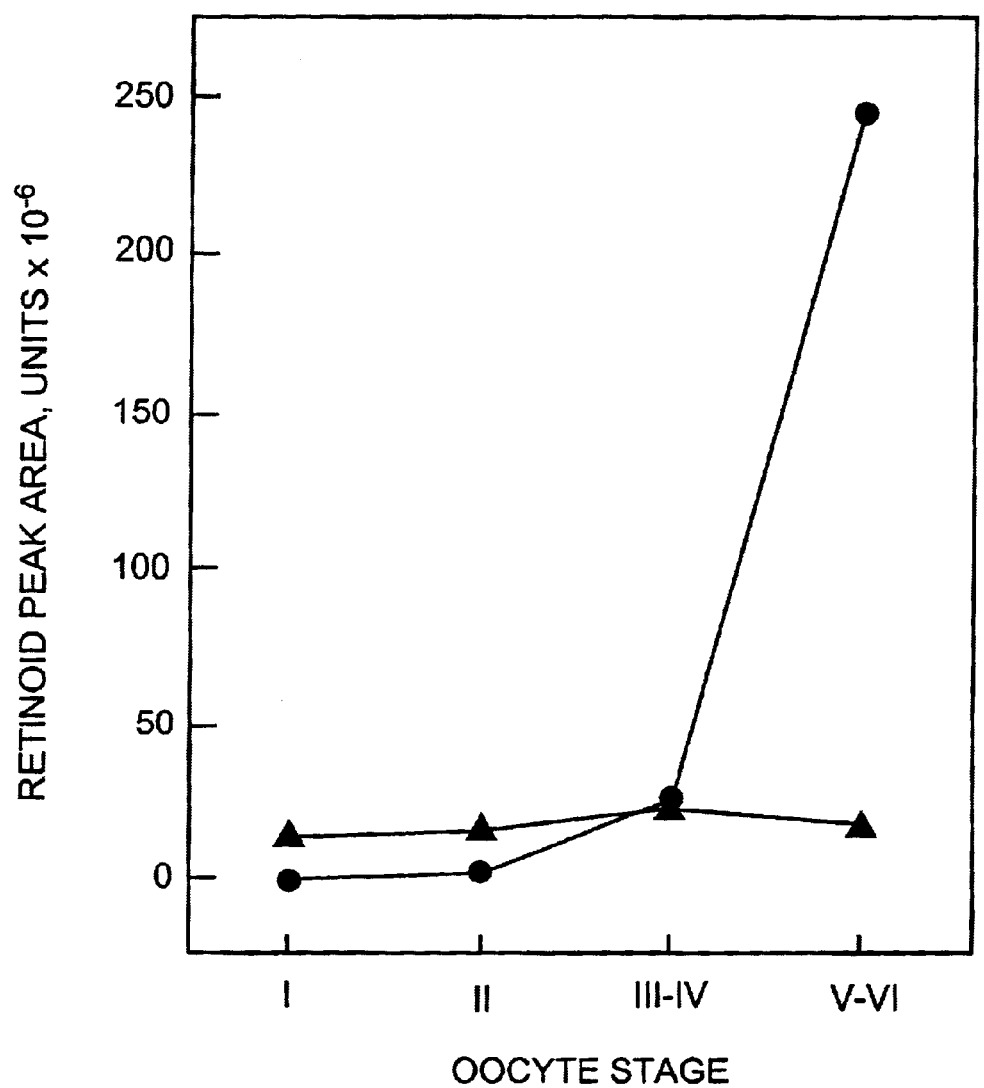
FIG. 2 depicts retinoid content of oocytes ay different stages of maturation. The only retinoid that accumulates progressively during oogenesis is the 4-oxo-retinyl ester (circles). The amounts of other retinoids remain constant. Only that of beta-carotene is shown for comparison (triangles).

The content of each of the retinoids and bilin in oocytes at different stages of maturation (I–VI) were compared (FIG. 2). Thus, stage I eggs are nearly devoid of bilin, however, as the oocytes mature, the bilin-containing fraction that elutes at 44.7% acetonitrile increases progressively and becomes maximal at state VI. In comparison, the retinoids do not accumulate. Their amounts remain essentially stable throughout oogenesis. Hence, the fraction that elutes with 44.7% acetonitrile is the only differeguline that preferentially and quantitatively accumulates as a function of oocyte maturation; it increases continuously during oogenesis and is stored in the mature oocyte.

Assignment of Chemical Structure

Figure 3A:
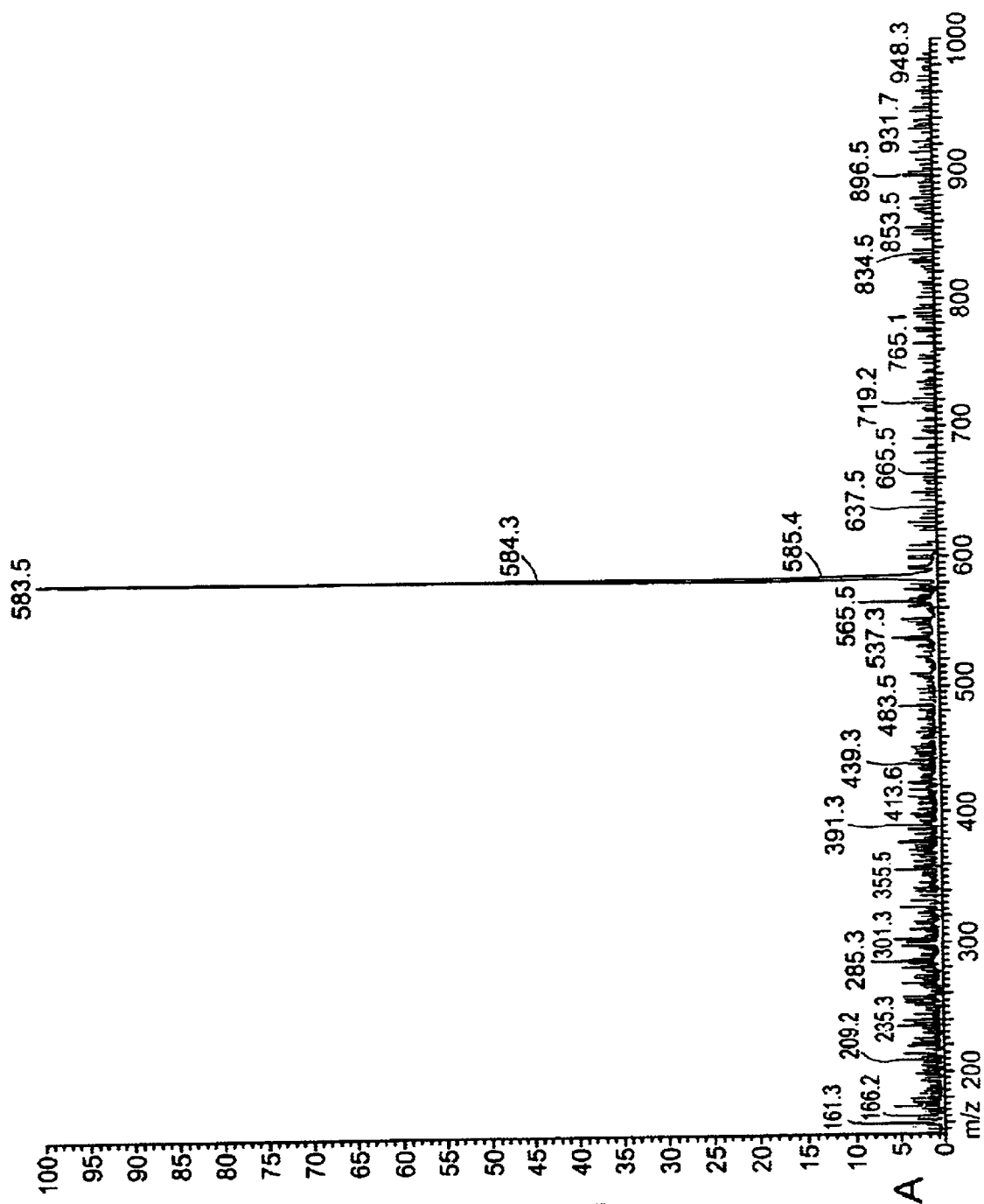
FIGS. 3–3B depict mass spectrometric analyses of the major oocyte retinoid. (A) shows a single peak of molecular mass 582 daltons observed upon analysis of the intact molecule. (B) shows the reagmentation pattern of the major oocyte retinoid which reveals two peaks of 297 and 566 daltons, consistent with loss of a water molecule from the intact species.
Figure 3B:
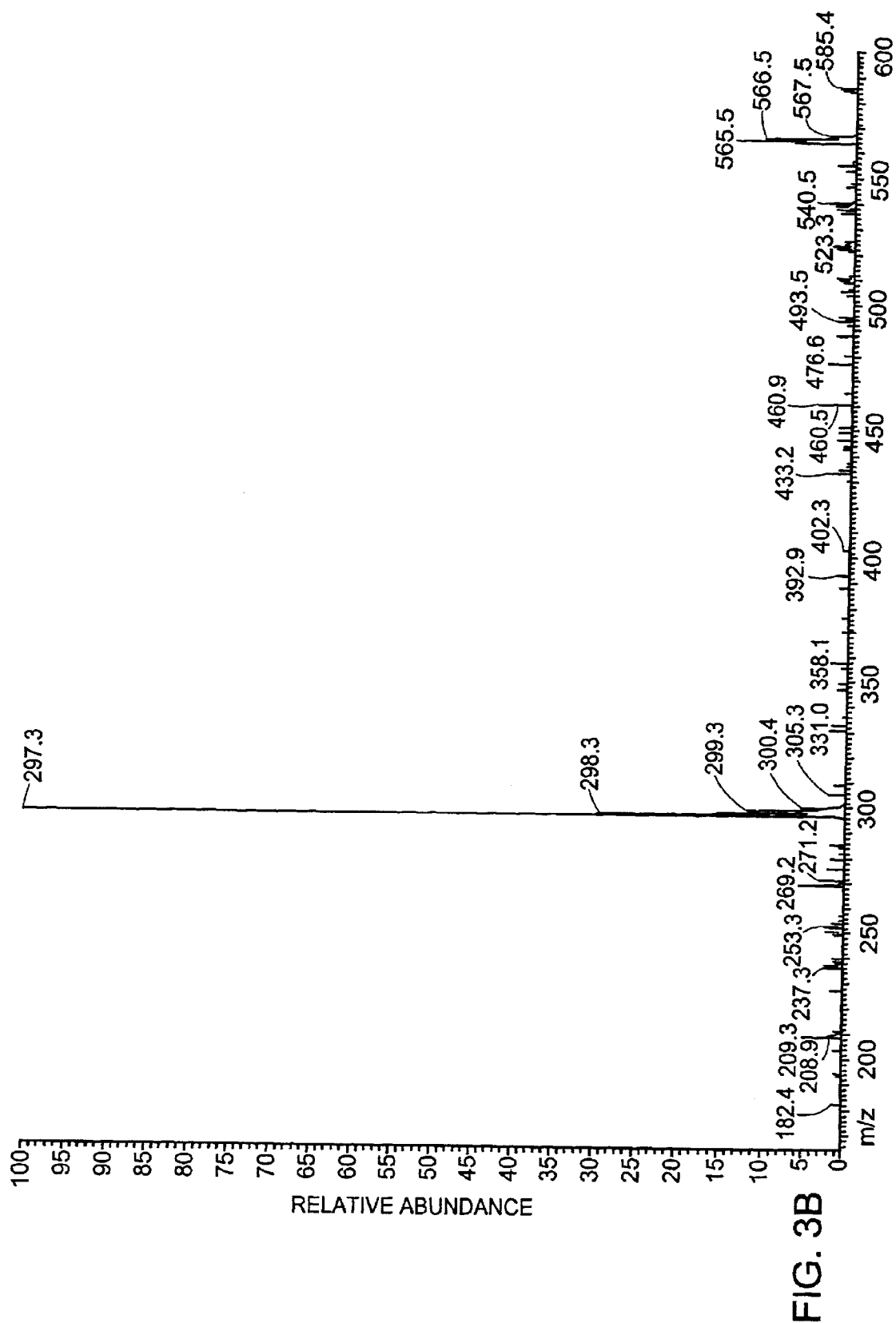
Figure 4:
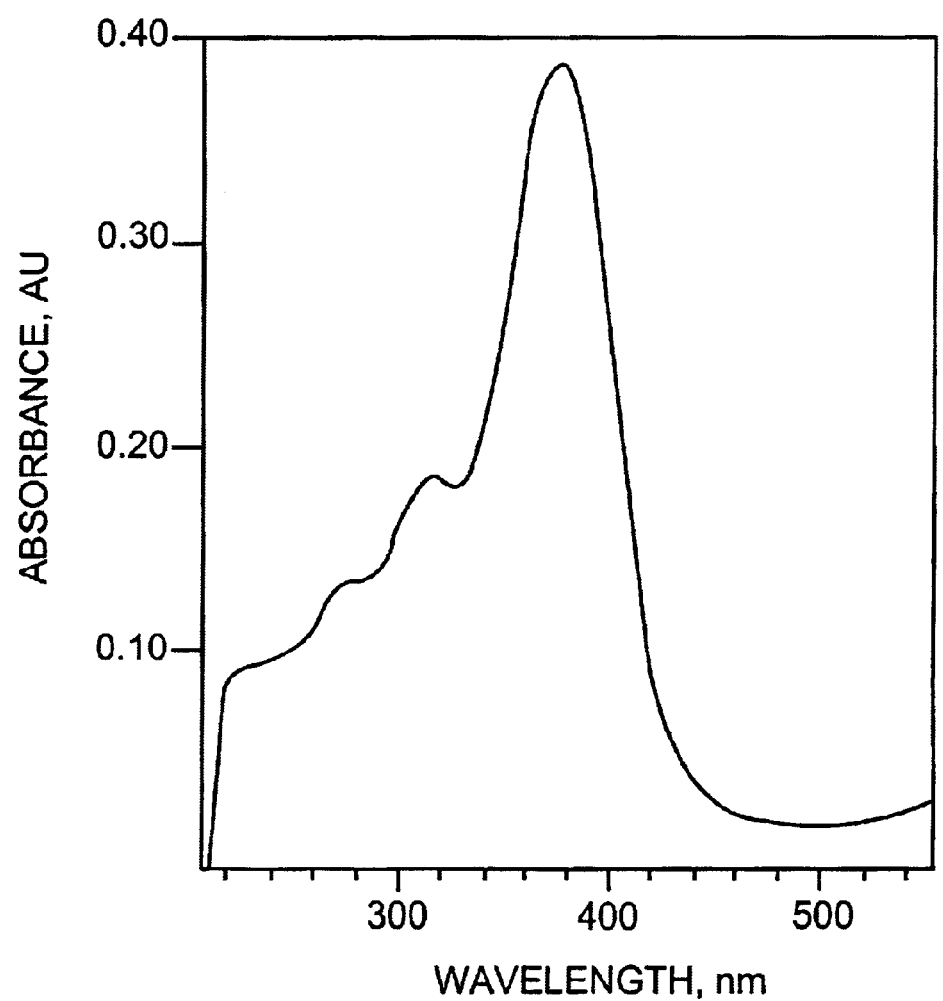
FIG. 4 depicts an absorption spectrum of the major oocyte retinoid. The 380 nm maximum is characteristic of a 4-oxo retinoid.

Mass spectrometric data reveals the material to be a single pure fraction with a molecular mass of 582 daltons (FIG. 3A). The single peak is fragmented into two species by mass spectrometric analysis (FIG. 3B). The heavier of the two species has a molecular mass of 565 daltons, consistent with loss of a water molecule from the native compound, while the other one is 297, consistent with loss of a species of molecular mass of 286. The absorption spectrum of this bilin fraction has a maximum at 380 nm (FIG. 4).

Kinetics of Utilization of Biliverdine in the Embryo

Figure 5:
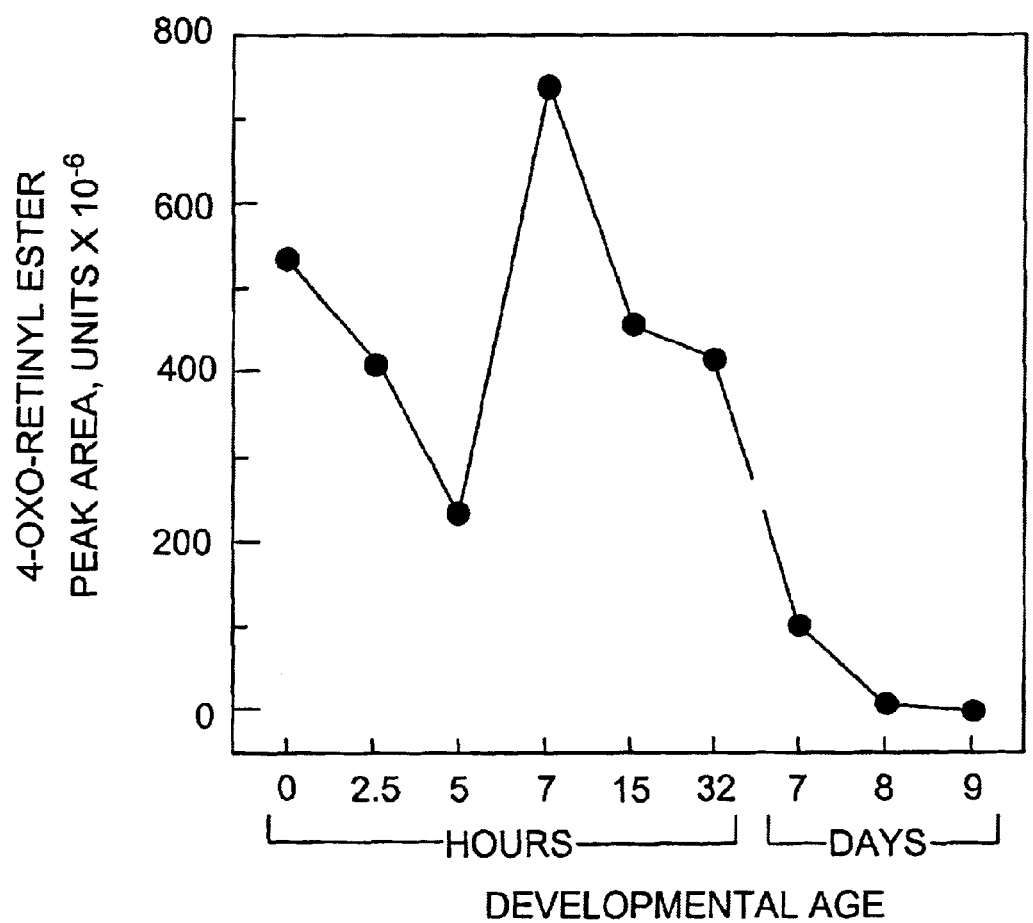
FIG. 5 depicts kinetics of utilization of the 4-oxo-retinyl ester during embryonic milestones.

The elution profile observed when extracts from embryos are chromatographed are quantitatively similar to that of oocytes (FIG. 1). The total peak area of biliverdine, however, undergoes changes during each embryonic milestone (FIG. 5). During the first 4 hours of embryogenesis, it decreases progressively until 60% of the material has disappeared. In early blastula stage, the fraction is repleted to the point that it returns to a level equal to or exceeding that of state VI oocyctes. This is associated with a decrease of those peaks corresponding to carotenes. Over the next 90 hours, the period of organogenesis, the amount of the material decreases once again until it eventually disappears.

When compared with the above quantitative changes in biliverdine, the variation in the total amount of each of the retinoids is minor during embryogenesis. This observation is similar to that noted during oogenesis (FIG. 2).

The adult frog liver, lung, and muscle contain a number of retinoids and precursors but do not contain biliverdine. The only adult tissue where this bilin is found is the ovary. Similar findings were obtained with oocyte extracts from albino frogs. Hence, the absence of pigment in the albino frogs did not result in differences in terms of the quantities and presences of biliverdine.

Distribution in Isopycnic Sucrose Gradient

Figure 6A:
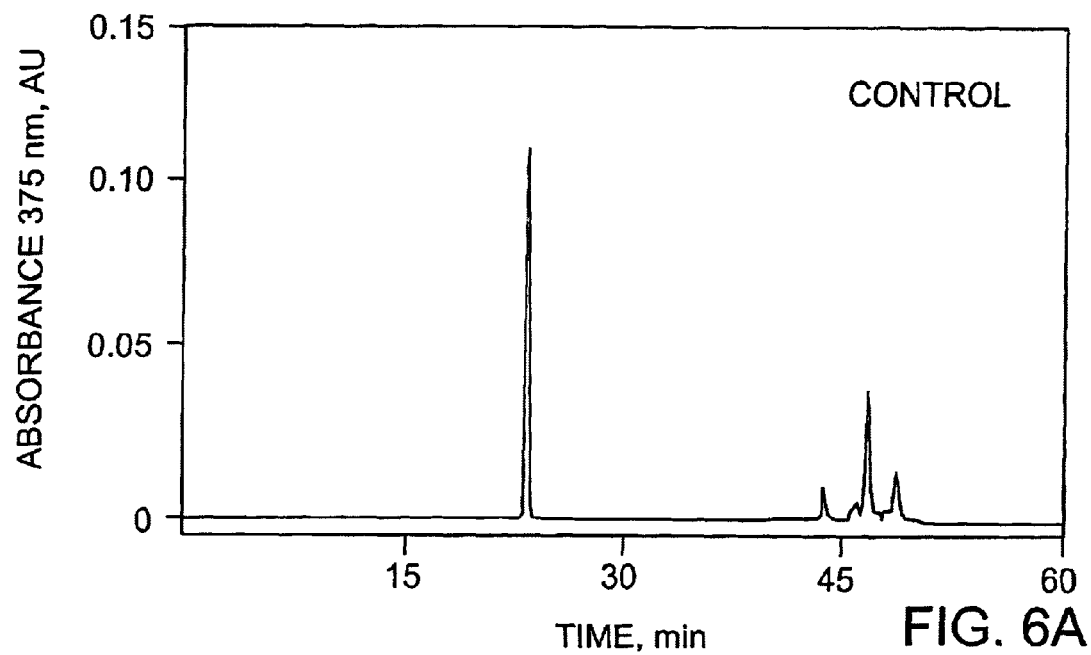
FIGS. 6A–6B depicts the effect of UV light on the content of the 4-oxo-retinyl ester (peak eluting at 23 minutes). (A) shows data from a control embryo and (B) shows data from a UV exposed embryo.
Figure 6B:
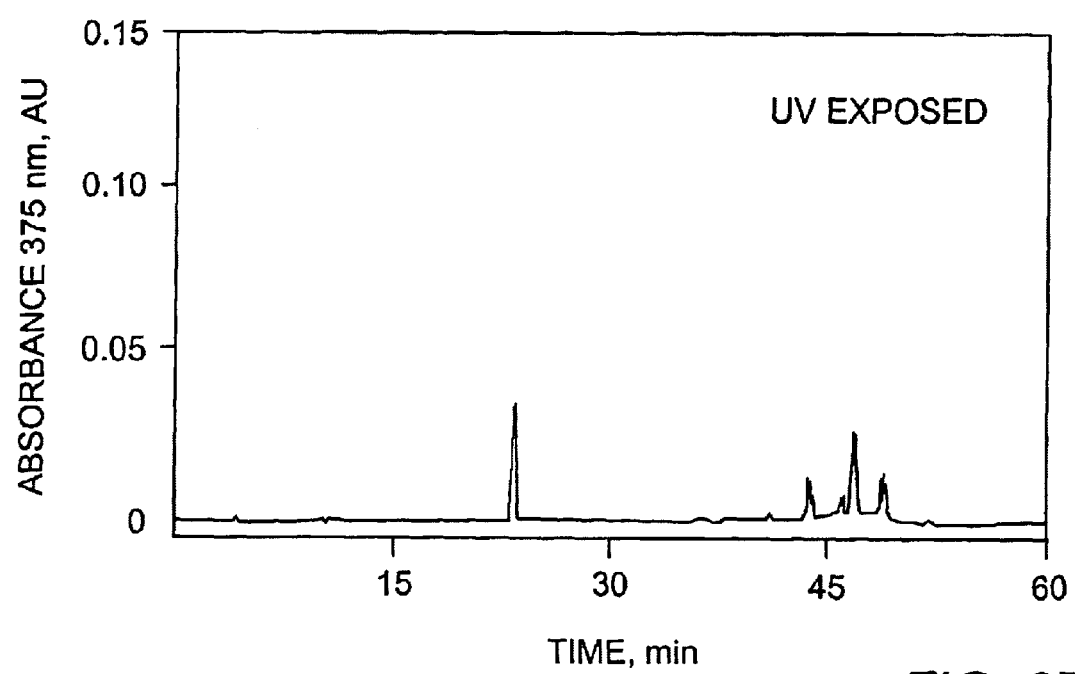

An oocyte homogenate separates on a standard sucrose gradient (1.08–1.24 g/ml) into fractions containing known components (81–83). The cytosol, ribonucleoprotein particles, and small endocytosed vesicles collect at densities between 1.08 to 1.12 g/ml while the multivesicular bodies collect at densities between 1.14 and 1.16 g/ml. The most predominant intracellular organelles are the yolk platelets, constituents that layer at densities of 1.20 to 1.24 g/ml. In general, light yolk platelets are found in the upper zones (1.20 g/ml) and heavier platelets in the lower zone (1.24 g/ml). The densest particles that centrifuge to the bottom of the gradient are the nuclei. The 8 fractions derived from oocyte homogenates fractionated by sucrose gradient centrifugation exhibit different physical characteristics. Fraction 1 was a whitish lipid-containing layer. Fractions 2 and 3 were clear, fraction 4 had a yellow band, fraction 5 was also clear, fractions 6 and 7 had the light beige color of platelets, and fraction 8 contained greenish pigment. The peaks comprising the entire bilin/retinoid profiles generated on chromatography of the homogenate extracts (FIG. 1) are recovered but now are distributed within the individual fractions of the sucrose gradient (FIG. 6). The upper layers of lightest sucrose densities (layers 1–4) contain mostly a single compound that elutes at 33 min. Biliverdine is not cystosolic but rather is entirely distributed in fractions 6, 7 and 8, co-sediment with oocyte vesicles and/or organelles including the light and heavy yolk platelets and nuclei. The relative abundance of this compound is highest in the light yolk platelet region.

TABLE I

Distribution of Biliverdine in Sucrose Gradient Fractions

| FRACTION | OOCYTE CONSTITUENT | Biliverdine |
|---|---|---|
| 1 | LIPIDS | Not Present |
| 2 | CYTOSOL | Not Present |
| 3 | CYTOSOL | Not Present |
| 4 | ENDOCYTOSED VESICLES | Not Present |
| 5 | MULTI VESICULAR BODIES AND MITOCHONDRIA | Not Present |
| 6 | LIGHT YOLK PLATELETS | +++ |
| 7 | HEAVY YOLK PLATELETS | ++ |
| 8 | NUCLEI | + |

Exposure of Embryos to Ultraviolet Light

The data establish that biliverdine is contained within oocyte nuclei, vesicles, granule, and/or yolk platelets. This provided us with the opportunity to examine whether destroying or altering the molecular structure of the bilin would affect embryogenesis. The platelets (and other granules) settle to the ventral hemisphere following fertilization and rotation (84). Exposure of the ventral surface to the pre-cleavage embryos to UV light is know to induce teratogenesis (85,86). To determine if there is a relationship between UV light exposure, biliverdine content in the ventral surface of the embryo, and subsequent teratology, we tested whether this irradiation affected biliverdine content of the exposed embryo.

The retinoid/bilin fractions eluting from the extracts of UV exposed embryos were compared to that of control embryos. Only one compound was found to decrease after UV irradiation, namely biliverdine; its content decreased by 50%. The only other change eluted at 43 min. In contrast, its peak area is increased. The relationship between these two fractions is to be determined. All other peaks were unchanged. See FIG. 6.

TABLE II

Effect of Ultraviolet Irradiation on Embryo Teratology

| Group | Total | Dead | Alive | Normal | Teratology |
|---|---|---|---|---|---|
| Control | 203 | 10 | 193 | 192 | 1 |
| n (%) | (100) | (5) | (100) | (99.5) | (0.5) |
| UV | 190 | 13 | 177 | 80 | 97 |
| n (%) | (100) | (7) | (100) | (45) | (55) |

Figure 7A:
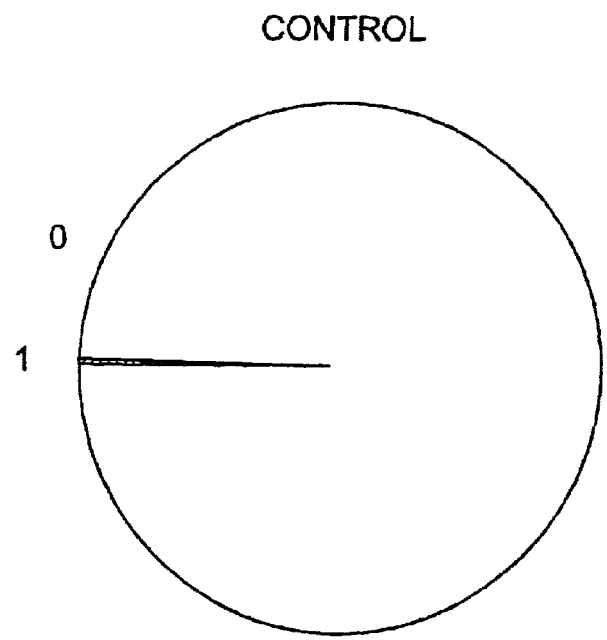
FIGS. 7A–7B depict the index of axial deficiency of embryos exposed to UV irradiation. (A) shows control embryos and (B) shows exposed embryos.
Figure 7B:
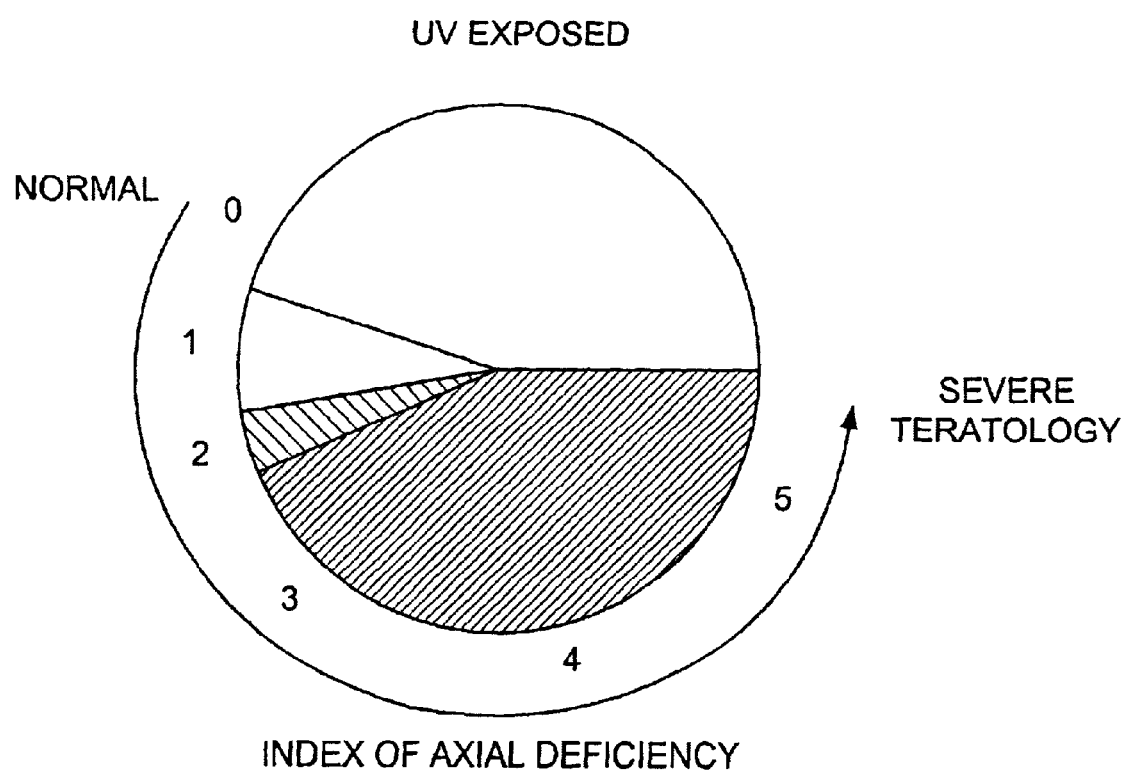

Of 203 control embryos, about 5% died within the first hour post-fertilization. Over 99% of the embryos developed normally; only 1/203 control embryos (0.5%) demonstrated teratology (Table II). In that case, the teratology was scored with an index of axis deficiency of [1], consistent with the expected (24, 25). In contrast, 97/190 of the UV irradiated embryos (55%) manifested the "UV syndrome" with the majority developing with index of axis deficiency of [4] or [5] (FIG. 7). In the irradiated group, the number of embryos that died in the first cell cycle was less than 7%, only slightly higher than the control group.

Biliverdine is a Biologically Active Inducer of Differentiation of HT29 Colon Cancer Cells The HT29 colon cancer cells were incubated with different concentrations of biliverdine and their response studied to identify the concentration ranges required to elicit a biological and/or a toxicological response (Table III).

TABLE III

Effects of Biliverdine on Cellular Proliferation and Viability.

| Concentration, $\mu$M | Effect |
|---|---|
| 0.01 | None |
| 0.1 | Proliferative Arrest |
| 0.30 | Proliferative Arrest |
| 0.40 | Proliferative Arrest |
| 1.00 | Apoptosis |

The effects of biliverdine on cell proliferation and production of two differentiation markers, CEA and alkaline phosphatase activity, were analyzed. CEA was assayed by standard ELISA determinations while alkaline phosphatase activity was determined by measuring the fluorescence change induced by the hydrolysis of phosphate from 4-methylumbelliferylphosphate as follows. To measure CEA production, cell supernatants were collected at the first cycle of change of media (third day) and on day 12. Cell counts were obtained. The supernatant was dried under vacuum using a Savant Speed Vac Plus. The residue was resuspended in 400 $\mu$l Milli-Q water. This was diluted 1:1 and assayed for CEA using an Imx assay for quantitive measurement of the antigen. The kit reagents were added to the sample and incubated to bind the CEA to anti-CEA coated micro particles. An aliquot was transferred to a glass matrix that binds the micro particles irreversibly. After washing, anti-CEA conjugated to alkaline phosphatase was added forming an additional complex to the CEA present in the reaction mixture. Following washing, the alkaline phosphatase substrate, 4-methylumbelliferyl phosphate, was added and the resultant fluorescence was read by a Micro particle Enzyme optical assembly.

Alkaline phosphatase activity was assayed at the same periods as above but with different sets of cells. Treated and control cells were detached with trypsin and counted. One half of the cells were used to maintain the culture while the other half were used to measure alkaline phosphatase activity. The cells were trypsinized and washed with phosphate buffered saline three times and lysed in 200 $\mu$l of Milli-Q water. Ten $\mu$l of the cell lysate were taken for determination of protein concentration using a Bio-Rad Protein Assay Kit (Bio-Rad). The aliquot was added to 800 and 190 $\mu$l of Milli-Q water and Coomassie blue dye, respectively. Absorbance was detected at 595 mm on a Varian Cary UV-Visible Spectrophotometer. The absorbance was compared against a standard curve created with bovine serum albumin from 2.5 to 25 $\mu$g/ml. Two hundred $\mu$l of incubation buffer containing the alkaline phosphatase substrate, 4-methylumbelliferyl phosphate in diethanolamine, 0.5 M, pH 10.4, was added to the remaining cell lysate. The mixture was incubated at 37° C. for 4 hrs after which 5.5 ml of ice cold amino-methyl propanol (AMP) buffer, pH 12, was added. The fluorescence generated is detected at 450 nm with an excitation of 365 nm, using a Jobin Ivon-Spex Fluoro Max-2 fluorimeter. The calibration curve was be generated from 0.05 to 50 $\mu$M. The alkaline phosphatase actively detected was expressed in units of $\mu$mol product/mg protein/min.

Figure 8:
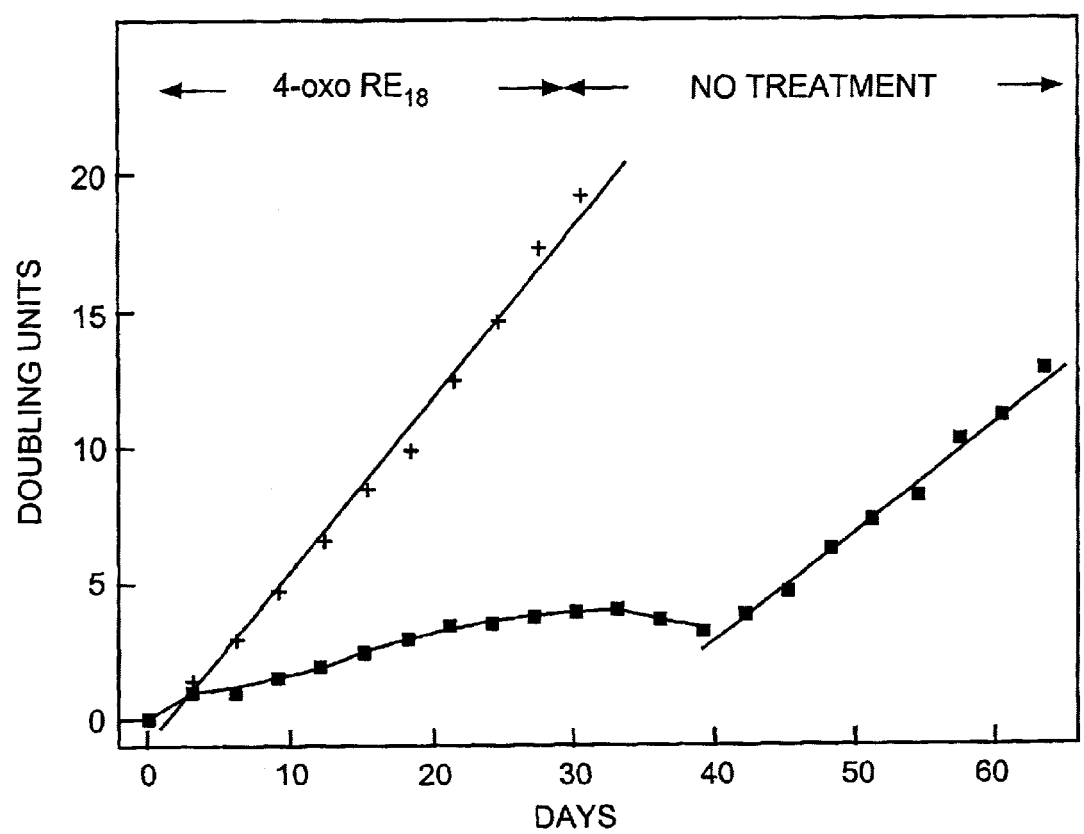
FIG. 8 depicts the effects of 4-oxoRE$_{18}$ on growth of HT29 cancer cells. Within three days of exposure, proliferation is arrested (boxes). On day 28, treatment is discontinued. Twelve days later, proliferation resumes at a rate that is 2.3× less than control (plus signs).
Figure 9:
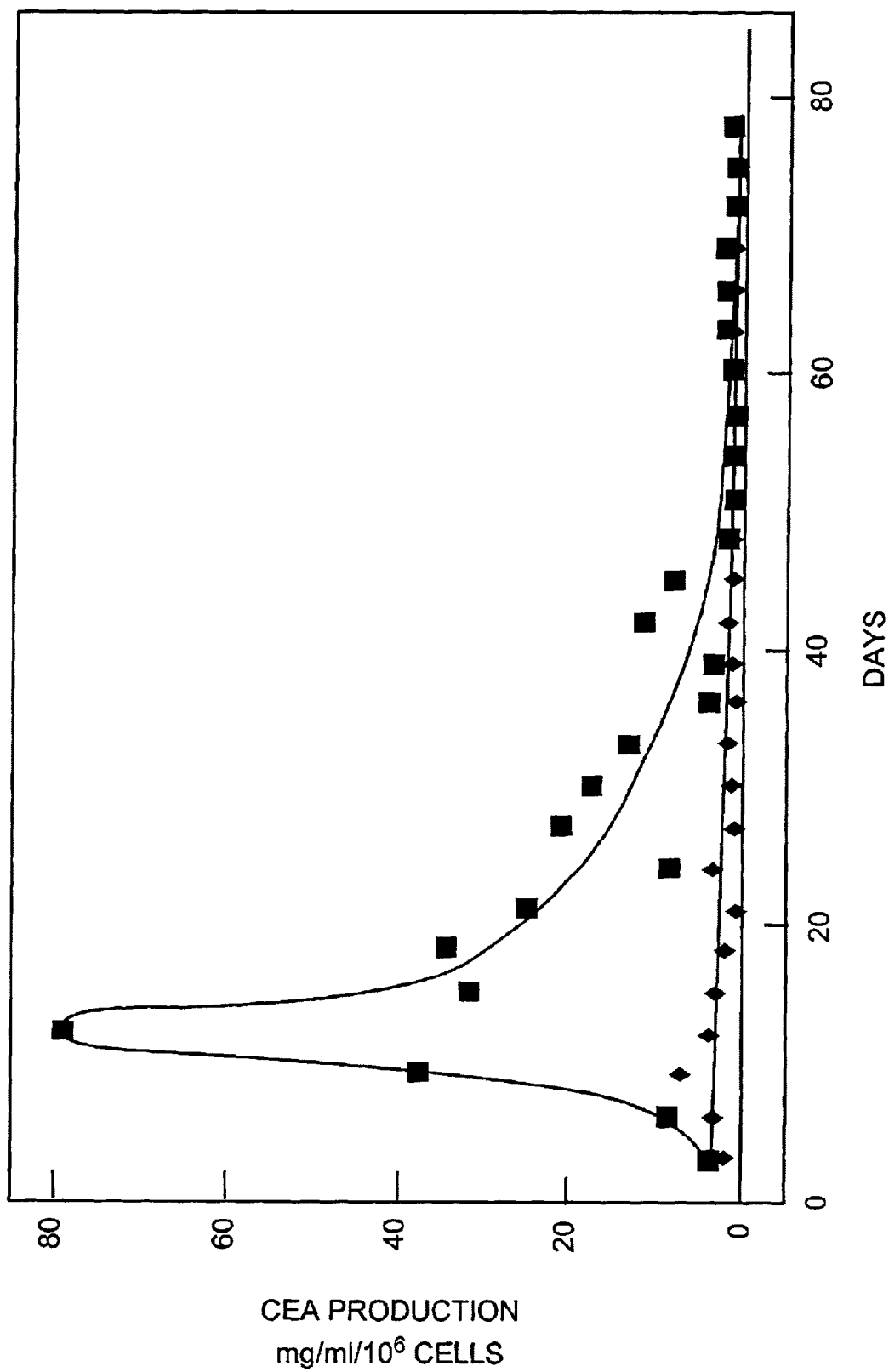
FIG. 9 depicts the effect of 4-oxoRB$_{18}$ on HT29 colon cancer cell CEA production. Treatment period is from 1–28 days. During the quiescent proliferative period, days 3–28, there is a 30-fold overproduction of the differentiation marker CEA. Its production returns to or below control prior to resumption of cell division (see FIG. 6).
Figure 11A:
FIGS. 11A–11E depict the results of experiments measuring the effect of UV exposure on embryo teratology.
Figure 11B:
Figure 11C:
Figure 11D:
Figure 11E:

At concentrations of 1 $\mu$M and above, biliverdine causes apoptosis while below 0.1 $\mu$M it has no effect on either survival or proliferation. Cells incubated with concentrations between 0.1 and 0.4 $\mu$M exhibit a proliferative arrest within the first 72 hours followed by a nearly complete inhibition of cell division (FIG. 8). The marked reduction in proliferation persists throughout exposure to the compound and for about 12 days after release of exposure. Only then does brisk proliferation resume, but at a rate that is much slower than that of control, untreated cells. Thus, control cells have a doubling rate of about 18 hrs, i.e., in a three-day period the number of cells increases about 15 times. The treated and released cells divide every 41 hrs, i.e., in a three-day period their number increases only 3.4 times, a five-fold reduction compared to the controls. The period of proliferative arrest, however, is not a metabolically quiescent stage, as determined by the change in the expression of two differentiation markers. The amounts of CEA produced were measured in the culture media removed routinely every third day when cells were subcultured. In the second period, day six of exposure, CEA increased over 30-fold and then decreased, reaching values comparable to that of media from control cells by the seventy period on day 21 (FIG. 9). Similar increases, though to lesser levels (fifteen-fold), are observed with alkaline phosphatase activity (FIG. 10).

All of the references cited above are hereby incorporated by reference herein.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method for promoting colon adenocarcinoma cell differentiation, comprising treating a colon adenocarcinoma cell with a bilin.

2. A method for promoting differentiation of a colon adenocarcinoma cell, comprising treating a colon adenocarcinoma cell with a bilin represented by the general formula (I):

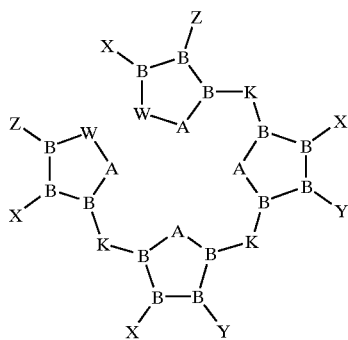

(I)

wherein

W represents —$CL_2$—, —C(=O)—, —C(=S)—, —C(=NH)—, or =CL—;

X represents a substituted or unsubstituted alkyl, alkenyl, or alkynyl group;

Y represents a substituted or unsubstituted alkyl, alkenyl, or alkynyl group;

Z represents a substituted or unsubstituted alkyl, alkenyl, or alkynyl group;

A represents —NH— or —N=;

B represents a trisubstituted, $sp^2$-hybridized carbon atom;

K represents =CL— or —$CL_2$—; and

L represents H or lower alkyl.

3. The method of claim 2, wherein the cell is contacted with the bilin in vitro.

4. The method of claim 2, wherein the cell is contacted with the bilin in vivo.

5. The method of claim 4, wherein the bilin is administered as part of a therapeutic application.

6. A method for promoting colon adenocarcinoma cell differentiation, comprising administering to a patient a pharmaceutical preparation comprising a sterile pharmaceutical excipient and a bilin.

7. The method of claim 1, wherein the bilin is bilirubin or biliverdine.

8. The method of claim 2, wherein the bilin is bilirubin or biliverdine.

9. A method for promoting colon adenocarcinoma cell differentiation, comprising administering to a patient a pharmaceutical preparation comprising a sterile pharmaceutical excipient and a bilin represented by the general formula (I):

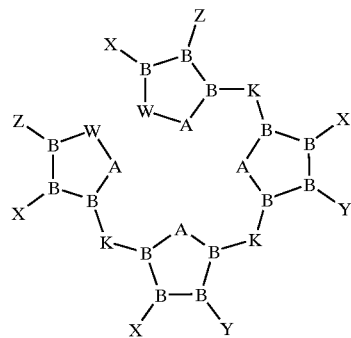

(I)

wherein

W represents —$CL_2$—, —C(=O)—, —C(=S)—, —C(=NH)—, or =CL—;

X represents a substituted or unsubstituted alkyl, alkenyl, or alkynyl group;

Y represents a substituted or unsubstituted alkyl, alkenyl, or alkynyl group;

Z represents a substituted or unsubstituted alkyl, alkenyl, or alkynyl group;

A represents —NH— or —N=;

B represents a trisubstituted, $sp^2$-hybridized carbon atom;

K represents =CL— or —$CL_2$—; and

L represents H or lower alkyl.

* * * * *